US010738116B2

(12) United States Patent
Fry et al.

(10) Patent No.: US 10,738,116 B2
(45) Date of Patent: Aug. 11, 2020

(54) DUAL SPECIFIC ANTI-CD22-ANTI-CD19 CHIMERIC ANTIGEN RECEPTORS

(71) Applicant: The United States of America, as represented by the Secretary, Department of Health and Human Services, Bethesda, MD (US)

(72) Inventors: Terry J. Fry, Bethesda, MD (US); Crystal L. Mackall, Stanford, CA (US); Rimas J. Orentas, Washington, DC (US); Waleed Haso, Boston, MA (US); Haiying Qin, Potomac, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 14 days.

(21) Appl. No.: 15/559,485

(22) PCT Filed: Mar. 18, 2016

(86) PCT No.: PCT/US2016/023055
§ 371 (c)(1),
(2) Date: Sep. 19, 2017

(87) PCT Pub. No.: WO2016/149578
PCT Pub. Date: Sep. 22, 2016

(65) Prior Publication Data
US 2018/0111992 A1    Apr. 26, 2018

Related U.S. Application Data

(60) Provisional application No. 62/135,442, filed on Mar. 19, 2015.

(51) Int. Cl.
| C07K 16/28 | (2006.01) |
| C07K 14/725 | (2006.01) |
| C07K 14/705 | (2006.01) |
| A61P 35/00 | (2006.01) |
| G01N 33/574 | (2006.01) |

(52) U.S. Cl.
CPC .......... *C07K 16/2803* (2013.01); *A61P 35/00* (2018.01); *C07K 14/7051* (2013.01); *C07K 14/70517* (2013.01); *C07K 14/70578* (2013.01); *G01N 33/57492* (2013.01); *C07K 2317/31* (2013.01); *C07K 2317/53* (2013.01); *C07K 2317/56* (2013.01); *C07K 2317/622* (2013.01); *C07K 2317/73* (2013.01); *C07K 2319/02* (2013.01); *C07K 2319/03* (2013.01)

(58) Field of Classification Search
CPC .................. C07K 14/7051; C07K 16/2803
See application file for complete search history.

(56) References Cited

U.S. PATENT DOCUMENTS

| 8,591,889 B2* | 11/2013 | Dimitrov | ........... C07K 16/2803 424/130.1 |
| 8,906,682 B2 | 12/2014 | June et al. | |
| 9,279,019 B2* | 3/2016 | Dimitrov | ........... C07K 16/2803 |
| 10,072,078 B2* | 9/2018 | Orentas | ............... A61K 39/0011 |
| 2013/0280220 A1 | 10/2013 | Ahmed et al. | |
| 2014/0274909 A1 | 9/2014 | Orentas et al. | |
| 2015/0038684 A1* | 2/2015 | Jensen | ............... C07K 16/2803 530/391.9 |

FOREIGN PATENT DOCUMENTS

| WO | WO 2013/059593 A1 | 4/2013 |
| WO | WO 2013/123061 A1 | 8/2013 |
| WO | WO 2014/065961 A1 | 5/2014 |
| WO | WO 2015/187528 A1 | 12/2015 |
| WO | WO 2018/213337 A1 | 11/2018 |

OTHER PUBLICATIONS

Lu et al., Biochem Biophys Res Comm 318:507-513 (Year: 2004).*
Hegde et al., "Combinational Targeting Offsets Antigen Escape and Enhances Effector Functions of Adoptively Transferred T Cells in Glioblastoma," *Molecular Therapy*, 21(11): 2087-2101 (Nov. 2013).
Qin et al., "Preclinical Development of Bivalent Chimeric Antigen Receptors Targeting Both CD19 and CD22," *Molecular Therapy: Oncolytics*, 11: 127-137 (Dec. 2018), includes supplementary material (total of 19 pages).
Bang et al., "HA22 (R490A) is a Recombinant Immunotoxin with Increased Antitumor Activity without an Increase in Animal Toxicity," *Clinical Cancer Research*, 11:1545-50, 2005.
Clay et al., "Efficient Transfer of a Tumor Antigen-Reactive TCR to Human Peripheral Blood Lymphocytes Confers Anti-Tumor Reactivity," *J. Immunol.*, 163: 507-513, 1999.
Grada et al., "TanCAR: A Novel Bispecific Chimeric Antigen Receptor for Cancer Immunotherapy," Molecular Therapy—Nucleic Acids, 2, e105, Jul. 2013.
Haso et al., "Anti-CD22-chimeric antigen receptors targeting B cell precursor acute lymphoblastic leukemia," *Blood*, 121(7): 1165-1174, Feb. 14, 2013, prepublished online Dec. 14, 2012.
International Preliminary Report on Patentability, PCT patent application PCT/US2016/023055, dated Sep. 28, 2017.

(Continued)

*Primary Examiner* — Jessica H Roark
(74) *Attorney, Agent, or Firm* — Leydig, Voit & Mayer, Ltd.

(57) ABSTRACT

The invention provides dual specific chimeric antigen receptors (CARs) having antigenic specificity for CD19 and CD22. Nucleic acids, recombinant expression vectors, host cells, populations of cells, and pharmaceutical compositions relating to the CARs are disclosed. Methods of detecting the presence of cancer in a mammal and methods of treating or preventing cancer in a mammal are also disclosed.

Figure 1:
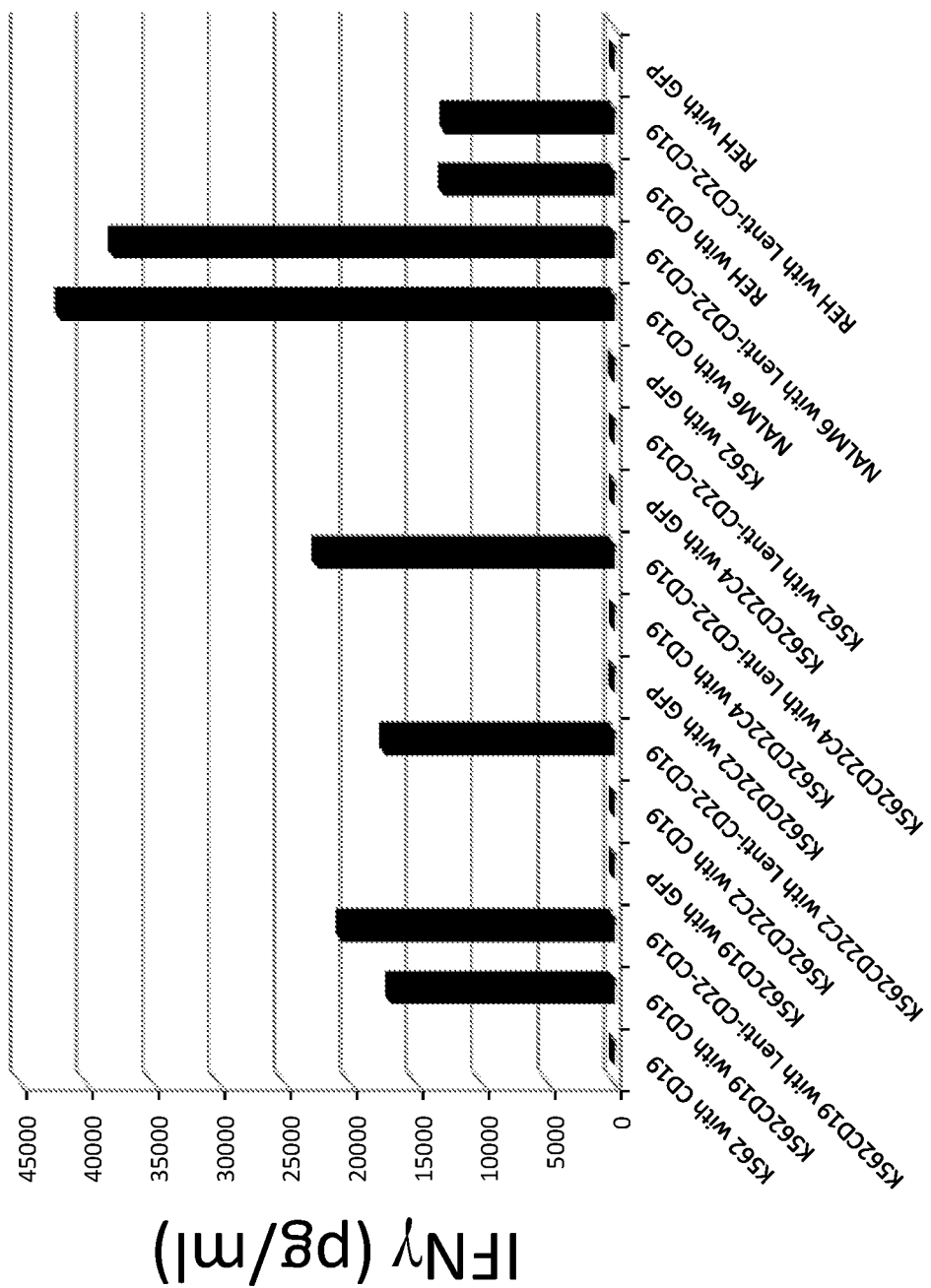
Figures 2A, 2B, 2C, 2D:
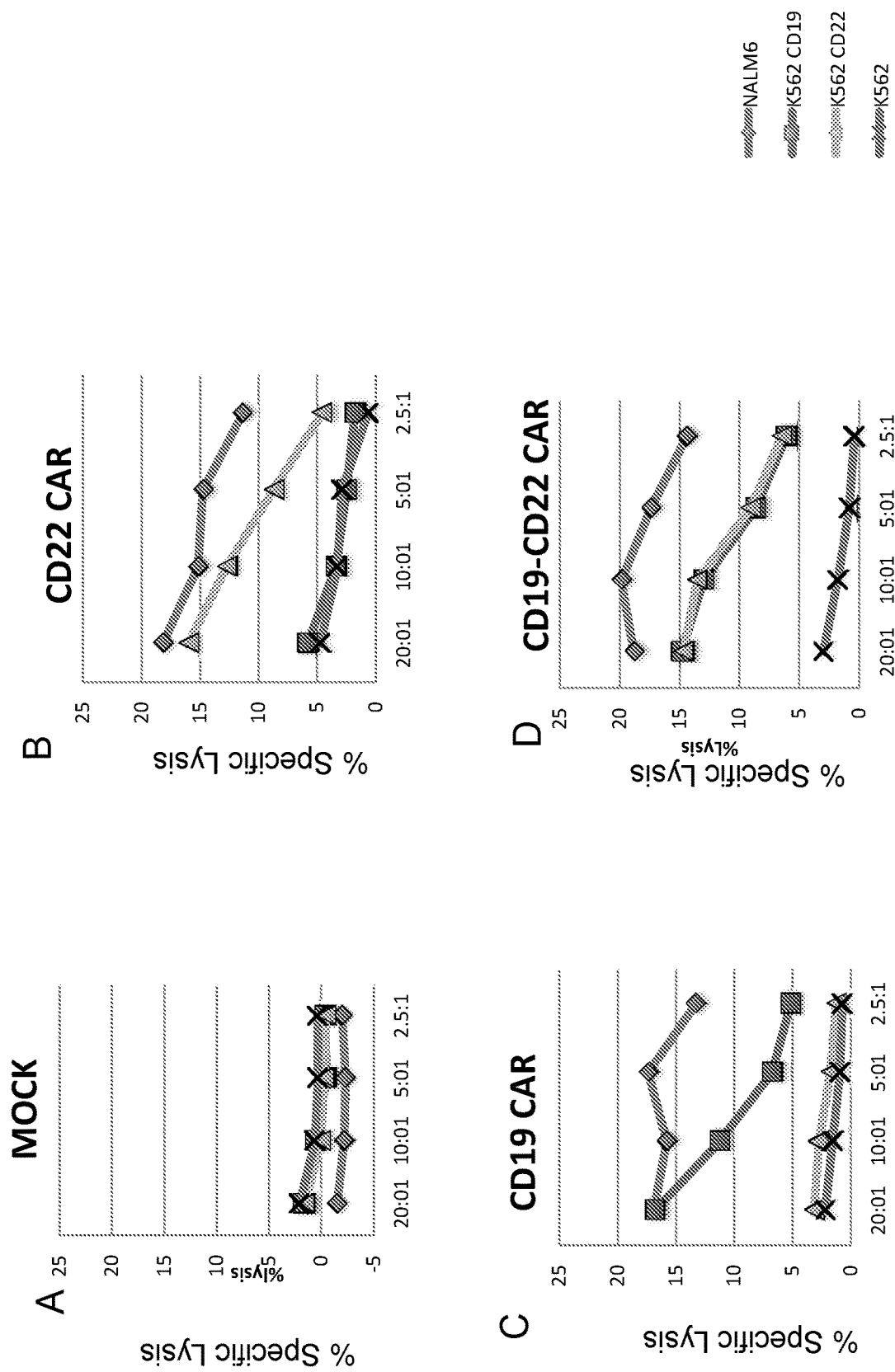

24 Claims, 5 Drawing Sheets
Specification includes a Sequence Listing.

(56) References Cited

OTHER PUBLICATIONS

International Search Report, PCT patent application PCT/US2016/023055, dated Jun. 17, 2016.
Lee et al., "T cells expressing CD19 chimeric antigen receptors for acute lymphoblastic leukaemia in children and young adults: a phase 1 dose-escalation trial," *Lancet*, pp. 1-12, S0140-6736 (14)61403-3, published online Oct. 13, 2014.
Long et al., "Lessons learned from a highly-active CD22-specific chimeric antigen receptor," *Oncoimmunology*, 2(4): 1-3, Apr. 2013.
Maude et al., "Chimeric Antigen Receptor T Cells for Sustained Remissions in Leukemia," *The New England Journal of Medicine*, 371 (16): 1507-17, Oct. 16, 2014.
Qin et al, "Novel CD19/CD22 Bicistronic Chimeric Antigen Receptors Outperform Single or Bivalent Cars in Eradicating CD19+CD22+, CD19- and CD22- Pre-B Leukemia," American Society of Hematology abstract 810 for oral presentation of Dec. 11, 2017; *Blood*, 130: 180, published Dec. 7, 2017 (1 page).
Qin, "Novel CD19/CD22 Multispecific Chimeric Antigen Receptor T cells for Treatment of Pre-B Leukemia," American Society of Hematology oral presentation, Dec. 11, 2017 (20 pages).
Qin et al, "Preclinical Development of Bispecific Chimeric Antigen Receptor Targeting Both CD19 and CD22", American Society of Hematology abstract 4427 for poster presentation of Dec. 7, 2015; *Blood*, 126: 4427, published Dec. 3, 2015 (1 page).
Qin, "Preclinical Development of Bispecific Chimeric Antigen Receptor Targeting Both CD19 and CD22," American Society of Hematology poster presentation, Dec. 7, 2015 (1 page).
Tedder et al., "Isolation of cDNAs encoding the CD19 antigen of human and mouse B lymphocytes. A new member of the immunoglobulin superfamily," *J. Immunol*, 143(2): 712-7, Jul. 15, 1989.
Vaickus et al., "Immune markers in hematologic malignancies," *Crit Rev Oncol Hematol*, 11(4): 267-97, Dec. 1991.
Written Opinion of the International Searching Authority (European Patent Office), PCT patent application PCT/US2016/023055, dated Jun. 17, 2016.
Zhao et al., "Primary Human Lymphocytes Transduced with NY-ESO-1 Antigen-Specific TCR Genes Recognize and Kill Diverse Human Tumor Cell Lines," *J. Immunol*. 174: 4415-4423, 2005.
Wu, "Diabodies: Molecular Engineering and Therapeutic Applications," *Drug News Perspect* 22(8):453-458 (Oct. 2009).

\* cited by examiner

SEQUENCE LISTING

```
<160> NUMBER OF SEQ ID NOS: 41

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Asp Ser Val Ser Ser Asn Ser Ala Ala
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Thr Tyr Tyr Arg Ser Lys Trp Tyr Asn
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Ala Arg Glu Val Thr Gly Asp Leu Glu Asp Ala Phe Asp Ile
1               5                   10
```

```
<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Gln Thr Ile Trp Ser Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic

<400> SEQUENCE: 5

Ala Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Ser Tyr Ser Ile Pro Gln Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Gly Val Ser Leu Pro Asp Tyr Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Ile Trp Gly Ser Glu Thr Thr
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

Ala Lys His Tyr Tyr Tyr Gly Gly Ser Tyr Ala Met Asp Tyr
1               5                   10
```

```
<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Gln Asp Ile Ser Lys Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic

<400> SEQUENCE: 11

His Thr Ser
1

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Gln Gln Gly Asn Thr Leu Pro Tyr Thr
1               5

<210> SEQ ID NO 13
<211> LENGTH: 124
<212> TYPE: PRT
<213> ORGANISM: Artificial Sequence
<220> FEATURE:
<223> OTHER INFORMATION: Synthetic

<400> SEQUENCE: 13

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: Synthetic
```

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Trp Ser Tyr
            20                  25                  30

Leu Asn Trp Tyr Gln Gln Arg Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Arg Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ile Pro Gln
                85                  90                  95

Thr Phe Gly Gln Gly Thr Lys Leu Glu Ile Lys
            100                 105

<210> SEQ ID NO 15
<211> LENGTH: 120
<212> TYPE: PRT
<213> ORGANISM: Artificial Sequence
<220> FEATURE:
<223> OTHER INFORMATION: Synthetic

<400> SEQUENCE: 15

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 16
<211> LENGTH: 107
<212> TYPE: PRT
<213> ORGANISM: Artificial Sequence
<220> FEATURE:
<223> OTHER INFORMATION: Synthetic

<400> SEQUENCE: 16

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 17
<211> LENGTH: 18
<212> TYPE: PRT
<213> ORGANISM: Artificial Sequence
<220> FEATURE:
<223> OTHER INFORMATION: Synthetic

<400> SEQUENCE: 17

Gly Ser Thr Ser Gly Ser Gly Lys Pro Gly Ser Gly Glu Gly Ser Thr
1               5                   10                  15

Lys Gly

<210> SEQ ID NO 18
<211> LENGTH: 25
<212> TYPE: PRT
<213> ORGANISM: Artificial Sequence
<220> FEATURE:
<223> OTHER INFORMATION: Synthetic

<400> SEQUENCE: 18

Gly Gly Gly Gly Ser Gly Gly Gly Ser Gly Gly Gly Ser Gly
1               5                   10                  15

Gly Gly Ser Gly Gly Gly Gly Ser
            20                  25

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Gly Gly Gly Gly Ser
1               5

<210> SEQ ID NO 20
<211> LENGTH: 249
<212> TYPE: PRT
<213> ORGANISM: Artificial Sequence
<220> FEATURE:
<223> OTHER INFORMATION: Synthetic

<400> SEQUENCE: 20

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Ser Thr Ser
            115                 120                 125

Gly Ser Gly Lys Pro Gly Ser Gly Glu Gly Ser Thr Lys Gly Asp Ile
        130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Thr Ile Trp Ser Tyr Leu Asn
                165                 170                 175

Trp Tyr Gln Gln Arg Pro Gly Lys Ala Pro Asn Leu Leu Ile Tyr Ala
            180                 185                 190

Ala Ser Ser Leu Gln Ser Gly Val Pro Ser Arg Phe Ser Gly Arg Gly
            195                 200                 205

Ser Gly Thr Asp Phe Thr Leu Thr Ile Ser Ser Leu Gln Ala Glu Asp
        210                 215                 220

Phe Ala Thr Tyr Tyr Cys Gln Gln Ser Tyr Ser Ile Pro Gln Thr Phe
225                 230                 235                 240

Gly Gln Gly Thr Lys Leu Glu Ile Lys
                245

<210> SEQ ID NO 21
<211> LENGTH: 236
<212> TYPE: PRT
<213> ORGANISM: Artificial Sequence
<220> FEATURE:
<223> OTHER INFORMATION: Synthetic

<400> SEQUENCE: 21

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
            115                 120                 125

Ser Asp Ile Gln Met Thr Gln Ser Pro Ser Ser Leu Ser Ala Ser Val
        130                 135                 140

Gly Asp Arg Val Thr Ile Thr Cys Arg Ala Ser Gln Thr Ile Trp Ser
145                 150                 155                 160

Tyr Leu Asn Trp Tyr Gln Gln Arg Pro Gly Lys Ala Pro Asn Leu Leu
                165                 170                 175

Ile Tyr Ala Ala Ser Ser Leu Gln Ser Gly Val Pro Ser Arg Phe Ser
            180                 185                 190

```
Gly Arg Gly Ser Gly Thr Asp Phe Thr Leu Thr Ile Ser Ser Leu Gln
            195                 200                 205

Ala Glu Asp Phe Ala Thr Tyr Tyr Cys Gln Gln Ser Tyr Ser Ile Pro
210                 215                 220

Gln Thr Phe Gly Gln Gly Thr Lys Leu Glu Ile Lys
225                 230                 235

<210> SEQ ID NO 22
<211> LENGTH: 245
<212> TYPE: PRT
<213> ORGANISM: Artificial Sequence
<220> FEATURE:
<223> OTHER INFORMATION: Synthetic

<400> SEQUENCE: 22

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 23
<211> LENGTH: 487
<212> TYPE: PRT
<213> ORGANISM: Artificial Sequence
<220> FEATURE:
<223> OTHER INFORMATION: Synthetic

<400> SEQUENCE: 23

Asp Ile Gln Met Thr Gln Thr Thr Ser Ser Leu Ser Ala Ser Leu Gly
1               5                   10                  15
```

-continued

```
Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
            50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
            85                  90                  95

Thr Phe Gly Gly Gly Thr Lys Leu Glu Ile Thr Gly Gly Gly Gly Ser
            100                 105                 110

Gln Val Gln Leu Gln Gln Ser Gly Pro Gly Leu Val Lys Pro Ser Gln
            115                 120                 125

Thr Leu Ser Leu Thr Cys Ala Ile Ser Gly Asp Ser Val Ser Ser Asn
            130                 135                 140

Ser Ala Ala Trp Asn Trp Ile Arg Gln Ser Pro Ser Arg Gly Leu Glu
145                 150                 155                 160

Trp Leu Gly Arg Thr Tyr Tyr Arg Ser Lys Trp Tyr Asn Asp Tyr Ala
            165                 170                 175

Val Ser Val Lys Ser Arg Ile Thr Ile Asn Pro Asp Thr Ser Lys Asn
            180                 185                 190

Gln Phe Ser Leu Gln Leu Asn Ser Val Thr Pro Glu Asp Thr Ala Val
            195                 200                 205

Tyr Tyr Cys Ala Arg Glu Val Thr Gly Asp Leu Glu Asp Ala Phe Asp
            210                 215                 220

Ile Trp Gly Gln Gly Thr Met Val Thr Val Ser Ser Gly Ser Thr Ser
225                 230                 235                 240

Gly Ser Gly Lys Pro Gly Ser Gly Glu Gly Ser Thr Lys Gly Asp Ile
            245                 250                 255

Gln Met Thr Gln Ser Pro Ser Ser Leu Ser Ala Ser Val Gly Asp Arg
            260                 265                 270

Val Thr Ile Thr Cys Arg Ala Ser Gln Thr Ile Trp Ser Tyr Leu Asn
            275                 280                 285

Trp Tyr Gln Gln Arg Pro Gly Lys Ala Pro Asn Leu Leu Ile Tyr Ala
            290                 295                 300

Ala Ser Ser Leu Gln Ser Gly Val Pro Ser Arg Phe Ser Gly Arg Gly
305                 310                 315                 320

Ser Gly Thr Asp Phe Thr Leu Thr Ile Ser Ser Leu Gln Ala Glu Asp
            325                 330                 335

Phe Ala Thr Tyr Tyr Cys Gln Gln Ser Tyr Ser Ile Pro Gln Thr Phe
            340                 345                 350

Gly Gln Gly Thr Lys Leu Glu Ile Lys Gly Gly Gly Ser Glu Val
            355                 360                 365

Lys Leu Gln Glu Ser Gly Pro Gly Leu Val Ala Pro Ser Gln Ser Leu
            370                 375                 380

Ser Val Thr Cys Thr Val Ser Gly Val Ser Leu Pro Asp Tyr Gly Val
385                 390                 395                 400

Ser Trp Ile Arg Gln Pro Pro Arg Lys Gly Leu Glu Trp Leu Gly Val
            405                 410                 415

Ile Trp Gly Ser Glu Thr Thr Tyr Tyr Asn Ser Ala Leu Lys Ser Arg
            420                 425                 430
```

Leu Thr Ile Ile Lys Asp Asn Ser Lys Ser Gln Val Phe Leu Lys Met
            435                 440                 445

Asn Ser Leu Gln Thr Asp Thr Ala Ile Tyr Tyr Cys Ala Lys His
        450                 455                 460

Tyr Tyr Tyr Gly Gly Ser Tyr Ala Met Asp Tyr Trp Gly Gln Gly Thr
465                 470                 475                 480

Ser Val Thr Val Ser Ser
                485

<210> SEQ ID NO 24
<211> LENGTH: 506
<212> TYPE: PRT
<213> ORGANISM: Artificial Sequence
<220> FEATURE:
<223> OTHER INFORMATION: Synthetic

<400> SEQUENCE: 24

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
        115                 120                 125

Ser Asp Ile Gln Met Thr Gln Ser Pro Ser Ser Leu Ser Ala Ser Val
130                 135                 140

Gly Asp Arg Val Thr Ile Thr Cys Arg Ala Ser Gln Thr Ile Trp Ser
145                 150                 155                 160

Tyr Leu Asn Trp Tyr Gln Gln Arg Pro Gly Lys Ala Pro Asn Leu Leu
                165                 170                 175

Ile Tyr Ala Ala Ser Ser Leu Gln Ser Gly Val Pro Ser Arg Phe Ser
            180                 185                 190

Gly Arg Gly Ser Gly Thr Asp Phe Thr Leu Thr Ile Ser Ser Leu Gln
        195                 200                 205

Ala Glu Asp Phe Ala Thr Tyr Tyr Cys Gln Gln Ser Tyr Ser Ile Pro
    210                 215                 220

Gln Thr Phe Gly Gln Gly Thr Lys Leu Glu Ile Lys Gly Gly Gly Gly
225                 230                 235                 240

Ser Gly Gly Gly Gly Ser Gly Gly Gly Ser Gly Gly Gly Gly Ser
                245                 250                 255

Gly Gly Gly Gly Ser Asp Ile Gln Met Thr Gln Thr Thr Ser Ser Leu
            260                 265                 270

Ser Ala Ser Leu Gly Asp Arg Val Thr Ile Ser Cys Arg Ala Ser Gln
        275                 280                 285

Asp Ile Ser Lys Tyr Leu Asn Trp Tyr Gln Gln Lys Pro Asp Gly Thr
    290                 295                 300

Val Lys Leu Leu Ile Tyr His Thr Ser Arg Leu His Ser Gly Val Pro
305                 310                 315                 320

Ser Arg Phe Ser Gly Ser Gly Ser Gly Thr Asp Tyr Ser Leu Thr Ile
            325                 330                 335

Ser Asn Leu Glu Gln Glu Asp Ile Ala Thr Tyr Phe Cys Gln Gln Gly
            340                 345                 350

Asn Thr Leu Pro Tyr Thr Phe Gly Gly Gly Thr Lys Leu Glu Ile Thr
            355                 360                 365

Gly Ser Thr Ser Gly Ser Gly Lys Pro Gly Ser Gly Glu Gly Ser Thr
        370                 375                 380

Lys Gly Glu Val Lys Leu Gln Glu Ser Gly Pro Gly Leu Val Ala Pro
385                 390                 395                 400

Ser Gln Ser Leu Ser Val Thr Cys Thr Val Ser Gly Val Ser Leu Pro
            405                 410                 415

Asp Tyr Gly Val Ser Trp Ile Arg Gln Pro Pro Arg Lys Gly Leu Glu
            420                 425                 430

Trp Leu Gly Val Ile Trp Gly Ser Glu Thr Thr Tyr Tyr Asn Ser Ala
        435                 440                 445

Leu Lys Ser Arg Leu Thr Ile Ile Lys Asp Asn Ser Lys Ser Gln Val
450                 455                 460

Phe Leu Lys Met Asn Ser Leu Gln Thr Asp Asp Thr Ala Ile Tyr Tyr
465                 470                 475                 480

Cys Ala Lys His Tyr Tyr Tyr Gly Gly Ser Tyr Ala Met Asp Tyr Trp
            485                 490                 495

Gly Gln Gly Thr Ser Val Thr Val Ser Ser
        500                 505

<210> SEQ ID NO 25
<211> LENGTH: 22
<212> TYPE: PRT
<213> ORGANISM: Artificial Sequence
<220> FEATURE:
<223> OTHER INFORMATION: Synthetic

<400> SEQUENCE: 25

Met Leu Leu Leu Val Thr Ser Leu Leu Cys Glu Leu Pro His Pro
1               5                   10                  15

Ala Phe Leu Leu Ile Pro
            20

<210> SEQ ID NO 26
<211> LENGTH: 24
<212> TYPE: PRT
<213> ORGANISM: Artificial Sequence
<220> FEATURE:
<223> OTHER INFORMATION: Synthetic

<400> SEQUENCE: 26

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 27
<211> LENGTH: 42
<212> TYPE: PRT
<213> ORGANISM: Artificial Sequence
<220> FEATURE:
<223> OTHER INFORMATION: Synthetic

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 28
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Xaa at position 14 may be Lys or Gln

<400> SEQUENCE: 28

Arg Val Lys Phe Ser Arg Ser Ala Asp Ala Pro Ala Tyr Xaa Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 29
<211> LENGTH: 711
<212> TYPE: PRT
<213> ORGANISM: Artificial Sequence
<220> FEATURE:
<223> OTHER INFORMATION: Synthetic

<400> SEQUENCE: 29

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gln Val Gln Leu Gln Gln Ser Gly Pro Gly Leu Val Lys Pro Ser Gln
        115                 120                 125

```
Thr Leu Ser Leu Thr Cys Ala Ile Ser Gly Asp Ser Val Ser Ser Asn
        130                 135                 140

Ser Ala Ala Trp Asn Trp Ile Arg Gln Ser Pro Ser Arg Gly Leu Glu
145                 150                 155                 160

Trp Leu Gly Arg Thr Tyr Tyr Arg Ser Lys Trp Tyr Asn Asp Tyr Ala
                165                 170                 175

Val Ser Val Lys Ser Arg Ile Thr Ile Asn Pro Asp Thr Ser Lys Asn
                180                 185                 190

Gln Phe Ser Leu Gln Leu Asn Ser Val Thr Pro Glu Asp Thr Ala Val
            195                 200                 205

Tyr Tyr Cys Ala Arg Glu Val Thr Gly Asp Leu Glu Asp Ala Phe Asp
210                 215                 220

Ile Trp Gly Gln Gly Thr Met Val Thr Val Ser Ser Gly Ser Thr Ser
225                 230                 235                 240

Gly Ser Gly Lys Pro Gly Ser Gly Glu Gly Ser Thr Lys Gly Asp Ile
                245                 250                 255

Gln Met Thr Gln Ser Pro Ser Ser Leu Ser Ala Ser Val Gly Asp Arg
                260                 265                 270

Val Thr Ile Thr Cys Arg Ala Ser Gln Thr Ile Trp Ser Tyr Leu Asn
            275                 280                 285

Trp Tyr Gln Gln Arg Pro Gly Lys Ala Pro Asn Leu Leu Ile Tyr Ala
        290                 295                 300

Ala Ser Ser Leu Gln Ser Gly Val Pro Ser Arg Phe Ser Gly Arg Gly
305                 310                 315                 320

Ser Gly Thr Asp Phe Thr Leu Thr Ile Ser Ser Leu Gln Ala Glu Asp
                325                 330                 335

Phe Ala Thr Tyr Tyr Cys Gln Gln Ser Tyr Ser Ile Pro Gln Thr Phe
                340                 345                 350

Gly Gln Gly Thr Lys Leu Glu Ile Lys Gly Gly Gly Ser Glu Val
            355                 360                 365

Lys Leu Gln Glu Ser Gly Pro Gly Leu Val Ala Pro Ser Gln Ser Leu
        370                 375                 380

Ser Val Thr Cys Thr Val Ser Gly Val Ser Leu Pro Asp Tyr Gly Val
385                 390                 395                 400

Ser Trp Ile Arg Gln Pro Pro Arg Lys Gly Leu Glu Trp Leu Gly Val
                405                 410                 415

Ile Trp Gly Ser Glu Thr Thr Tyr Tyr Asn Ser Ala Leu Lys Ser Arg
                420                 425                 430

Leu Thr Ile Ile Lys Asp Asn Ser Lys Ser Gln Val Phe Leu Lys Met
            435                 440                 445

Asn Ser Leu Gln Thr Asp Asp Thr Ala Ile Tyr Tyr Cys Ala Lys His
        450                 455                 460

Tyr Tyr Tyr Gly Gly Ser Tyr Ala Met Asp Tyr Trp Gly Gln Gly Thr
465                 470                 475                 480

Ser Val Thr Val Ser Ser Ser Gly Thr Thr Thr Pro Ala Pro Arg Pro
                485                 490                 495

Pro Thr Pro Ala Pro Thr Ile Ala Ser Gln Pro Leu Ser Leu Arg Pro
            500                 505                 510

Glu Ala Cys Arg Pro Ala Ala Gly Gly Ala Val His Thr Arg Gly Leu
        515                 520                 525

Asp Phe Ala Cys Asp Ile Tyr Ile Trp Ala Pro Leu Ala Gly Thr Cys
530                 535                 540
```

```
Gly Val Leu Leu Leu Ser Leu Val Ile Thr Leu Tyr Cys Lys Arg Gly
545                 550                 555                 560

Arg Lys Lys Leu Leu Tyr Ile Phe Lys Gln Pro Phe Met Arg Pro Val
                565                 570                 575

Gln Thr Thr Gln Glu Glu Asp Gly Cys Ser Cys Arg Phe Pro Glu Glu
                580                 585                 590

Glu Glu Gly Gly Cys Glu Leu Arg Val Lys Phe Ser Arg Ser Ala Asp
            595                 600                 605

Ala Pro Ala Tyr Lys Gln Gly Gln Asn Gln Leu Tyr Asn Glu Leu Asn
        610                 615                 620

Leu Gly Arg Arg Glu Glu Tyr Asp Val Leu Asp Lys Arg Arg Gly Arg
625                 630                 635                 640

Asp Pro Glu Met Gly Gly Lys Pro Arg Arg Lys Asn Pro Gln Glu Gly
                645                 650                 655

Leu Tyr Asn Glu Leu Gln Lys Asp Lys Met Ala Glu Ala Tyr Ser Glu
                660                 665                 670

Ile Gly Met Lys Gly Glu Arg Arg Arg Gly Lys Gly His Asp Gly Leu
                675                 680                 685

Tyr Gln Gly Leu Ser Thr Ala Thr Lys Asp Thr Tyr Asp Ala Leu His
690                 695                 700

Met Gln Ala Leu Pro Pro Arg
705                 710

<210> SEQ ID NO 30
<211> LENGTH: 729
<212> TYPE: PRT
<213> ORGANISM: Artificial Sequence
<220> FEATURE:
<223> OTHER INFORMATION: Synthetic

<400> SEQUENCE: 30

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
        115                 120                 125

Ser Asp Ile Gln Met Thr Gln Ser Pro Ser Ser Leu Ser Ala Ser Val
130                 135                 140

Gly Asp Arg Val Thr Ile Thr Cys Arg Ala Ser Gln Thr Ile Trp Ser
145                 150                 155                 160

Tyr Leu Asn Trp Tyr Gln Gln Arg Pro Gly Lys Ala Pro Asn Leu Leu
                165                 170                 175

Ile Tyr Ala Ala Ser Ser Leu Gln Ser Gly Val Pro Ser Arg Phe Ser
            180                 185                 190
```

```
Gly Arg Gly Ser Gly Thr Asp Phe Thr Leu Thr Ile Ser Ser Leu Gln
            195                 200                 205

Ala Glu Asp Phe Ala Thr Tyr Tyr Cys Gln Gln Ser Tyr Ser Ile Pro
210                 215                 220

Gln Thr Phe Gly Gln Gly Thr Lys Leu Glu Ile Lys Gly Gly Gly Gly
225                 230                 235                 240

Ser Gly Gly Gly Gly Ser Gly Gly Gly Gly Ser Gly Gly Gly Gly Ser
                245                 250                 255

Gly Gly Gly Gly Ser Asp Ile Gln Met Thr Gln Thr Thr Ser Ser Leu
            260                 265                 270

Ser Ala Ser Leu Gly Asp Arg Val Thr Ile Ser Cys Arg Ala Ser Gln
        275                 280                 285

Asp Ile Ser Lys Tyr Leu Asn Trp Tyr Gln Gln Lys Pro Asp Gly Thr
290                 295                 300

Val Lys Leu Leu Ile Tyr His Thr Ser Arg Leu His Ser Gly Val Pro
305                 310                 315                 320

Ser Arg Phe Ser Gly Ser Gly Ser Gly Thr Asp Tyr Ser Leu Thr Ile
                325                 330                 335

Ser Asn Leu Glu Gln Glu Asp Ile Ala Thr Tyr Phe Cys Gln Gln Gly
            340                 345                 350

Asn Thr Leu Pro Tyr Thr Phe Gly Gly Gly Thr Lys Leu Glu Ile Thr
        355                 360                 365

Gly Ser Thr Ser Gly Ser Gly Lys Pro Gly Ser Gly Glu Gly Ser Thr
    370                 375                 380

Lys Gly Glu Val Lys Leu Gln Glu Ser Gly Pro Gly Leu Val Ala Pro
385                 390                 395                 400

Ser Gln Ser Leu Ser Val Thr Cys Thr Val Ser Gly Val Ser Leu Pro
                405                 410                 415

Asp Tyr Gly Val Ser Trp Ile Arg Gln Pro Pro Arg Lys Gly Leu Glu
            420                 425                 430

Trp Leu Gly Val Ile Trp Gly Ser Glu Thr Thr Tyr Tyr Asn Ser Ala
        435                 440                 445

Leu Lys Ser Arg Leu Thr Ile Ile Lys Asp Asn Ser Lys Ser Gln Val
450                 455                 460

Phe Leu Lys Met Asn Ser Leu Gln Thr Asp Asp Thr Ala Ile Tyr Tyr
465                 470                 475                 480

Cys Ala Lys His Tyr Tyr Gly Gly Ser Tyr Ala Met Asp Tyr Trp
                485                 490                 495

Gly Gln Gly Thr Ser Val Thr Val Ser Ser Thr Thr Pro Ala Pro
            500                 505                 510

Arg Pro Pro Thr Pro Ala Pro Thr Ile Ala Ser Gln Pro Leu Ser Leu
        515                 520                 525

Arg Pro Glu Ala Cys Arg Pro Ala Ala Gly Gly Ala Val His Thr Arg
530                 535                 540

Gly Leu Asp Phe Ala Cys Asp Ile Tyr Ile Trp Ala Pro Leu Ala Gly
545                 550                 555                 560

Thr Cys Gly Val Leu Leu Leu Ser Leu Val Ile Thr Leu Tyr Cys Lys
                565                 570                 575

Arg Gly Arg Lys Lys Leu Leu Tyr Ile Phe Lys Gln Pro Phe Met Arg
            580                 585                 590

Pro Val Gln Thr Thr Gln Glu Glu Asp Gly Cys Ser Cys Arg Phe Pro
        595                 600                 605

Glu Glu Glu Glu Gly Gly Cys Glu Leu Arg Val Lys Phe Ser Arg Ser
```

```
Ala Asp Ala Pro Ala Tyr Lys Gln Gly Gln Asn Gln Leu Tyr Asn Glu
625                 630                 635                 640

Leu Asn Leu Gly Arg Arg Glu Glu Tyr Asp Val Leu Asp Lys Arg Arg
            645                 650                 655

Gly Arg Asp Pro Glu Met Gly Gly Lys Pro Arg Arg Lys Asn Pro Gln
                660                 665                 670

Glu Gly Leu Tyr Asn Glu Leu Gln Lys Asp Lys Met Ala Glu Ala Tyr
        675                 680                 685

Ser Glu Ile Gly Met Lys Gly Glu Arg Arg Arg Gly Lys Gly His Asp
    690                 695                 700

Gly Leu Tyr Gln Gly Leu Ser Thr Ala Thr Lys Asp Thr Tyr Asp Ala
705                 710                 715                 720

Leu His Met Gln Ala Leu Pro Pro Arg
                725

<210> SEQ ID NO 31
<211> LENGTH: 2208
<212> TYPE: DNA
<213> ORGANISM: Artificial Sequence
<220> FEATURE:
<223> OTHER INFORMATION: Synthetic

<400> SEQUENCE: 31
gccaccatgc tgctgctcgt gacaagcctg ctgctgtgcg agctgccca  cccctgccttt    60 ctgctgatcc ccgacatcca gatgacccag accaccagca gcctgagcgc cagcctgggc   120
gatagagtga ccatcagctg cagagccagc caggacatca gcaagtacct gaactggtat   180
cagcagaaac ccgacggcac cgtgaagctg ctgatctacc acaccagcag actgcacagc   240
ggcgtgccca gcagattttc tggcagcggc tccggcaccg actacagcct gaccatctcc   300
aacctggaac aggaagatat cgctacctac ttctgtcagc aaggcaacac cctgccctac   360
accttcggcg gaggcaccaa gctggaaatc acaggcggcg aggatcccca ggtgcagctg   420
cagcagtctg gacccggcct cgtgaagcct agccagaccc tgtctctgac ctgcgccatc   480
agcggcgata gcgtgtccag caatagcgcc gcctggaact ggatccggca gagcccttct   540
agaggcctgg aatggctggg ccggacctac taccggtcca agtggtacaa cgactacgcc   600
gtgtccgtga agtcccggat caccatcaac ccgacacca gcaagaacca gttctccctg   660
cagctgaaca gcgtgacccc cgaggatacc gccgtgtact actgcgccag agaagtgacc   720
ggcgacctga agatgccttt cgacatctgg ggccagggca atggtcac cgtgtctagc   780 ggcagcacaa gcggctctgg caagcctgga tctggcgagg gctctaccaa gggcgatatt   840
cagatgacac agagccccte cagcctgtcc gcctctgtgg gagacagagt gacaatcacc   900
tgtcgggcct cccagaccat ctggtcctat ctgaattggt atcagcagcg gcctggcaag   960 gccccccaacc tgctgatcta tgccgccagc tctctgcagt ccggcgtgcc atctagattc  1020
agcggcagag gcagcggcac cgatttcacc ctgacaatta gcagtctgca ggccgaggac  1080
ttcgccacct actattgcca gcagagctac agcatccccc cgaccttcgg ccagggaaca  1140
aaactggaaa tcaagggggg aggcggcagc gaagtgaaac tgcaggaatc tggccctggc  1200
ctggtggccc caagccagtc tctgagcgtg acctgtaccg tgtctggcgt gtccctgccc  1260
gattacggcg tgtcctggat cagacagccc cccagaaagg gactgaatg gctgggagtg  1320 atctggggca gcgagacaac ctactacaac agcgccctga gtccaggct gaccatcatc  1380
```

| | |
|---|---|
| aaggacaact ccaagagcca ggtgttcctg aagatgaatt ccctgcagac cgacgacacc | 1440 |
| gccatctatt actgtgccaa gcactactac tacggcggca gctacgccat ggactactgg | 1500 |
| ggacagggaa cctccgtgac cgtgtcctct tccggaacca cgacgccagc gccgcgacca | 1560 |
| ccaacaccgg cgcccaccat cgcgtcgcag cccctgtccc tgcgcccaga ggcgtgccgg | 1620 |
| ccagcggcgg ggggcgcagt gcacacgagg gggctggact tcgcctgtga tatctacatc | 1680 |
| tgggcgccct tggccgggac ttgtggggtc cttctcctgt cactggttat cacccttac | 1740 |
| tgcaaacggg gcagaaagaa actcctgtat atattcaaac aaccatttat gagaccagta | 1800 |
| caaactactc aagaggaaga tggctgtagc tgccgatttc cagaagaaga agaaggagga | 1860 |
| tgtgaactga gagtgaagtt cagcaggagc gcagacgccc ccgcgtacaa gcagggccag | 1920 |
| aaccagctct ataacgagct caatctagga cgaagagagg agtacgatgt tttggacaag | 1980 |
| agacgtggcc gggaccctga gatgggggga aagccgagaa ggaagaaccc tcaggaaggc | 2040 |
| ctgtacaatg aactgcagaa agataagatg cggaggcct acagtgagat tgggatgaaa | 2100 |
| ggcgagcgcc ggaggggcaa ggggcacgat ggcctttacc agggtctcag tacagccacc | 2160 |
| aaggacacct acgacgccct tcacatgcag gccctgcccc ctcgctaa | 2208 |

<210> SEQ ID NO 32
<211> LENGTH: 2262
<212> TYPE: DNA
<213> ORGANISM: Artificial Sequence
<220> FEATURE:
<223> OTHER INFORMATION: Synthetic

<400> SEQUENCE: 32

| | |
|---|---|
| gccaccatgc tgctgctcgt gacatctctg ctgctgtgcg agctgcccca ccccgccttt | 60 |
| ctgctgattc tcaggtgca gctgcagcag tctggccctg gcctcgtgaa gcctagccag | 120 |
| accctgagcc tgacctgtgc catcagcggc gatagcgtgt ccagcaatag cgccgcctgg | 180 |
| aactggatca gacagagccc tagcagaggc ctggaatggc tgggccggac ctactaccgg | 240 |
| tccaagtggt acaacgacta cgccgtgtcc gtgaagtccc ggatcaccat caaccccgac | 300 |
| accagcaaga accagttctc cctgcagctg aacagcgtga ccccgagga taccgccgtg | 360 |
| tactactgcg ccagagaagt gaccggcgac ctggaagatg ccttcgacat ctggggccag | 420 |
| ggcacaatgg tcaccgtgtc tagcggaggc ggcggaagcg acatccagat gacacagagc | 480 |
| cccagctccc tgagcgccag cgtgggagac agagtgacca tcacctgtcg ggccagccag | 540 |
| accatctggt cctacctgaa ctggtatcag cagcggcctg gcaaggcccc caacctgctg | 600 |
| atctatgccg ccagctcact gcagagcggc gtgcccagca gatttccgg cagaggcagc | 660 |
| ggcaccgact tcaccctgac aatcagttcc ctgcaggccg aggacttcgc cacctactac | 720 |
| tgccagcaga gctacagcat cccccagacc ttcggccagg gaccaagct ggaaatcaag | 780 |
| ggcgaggggg gatctggcgg cggaggatct ggggaggcg gcagtggggg cggaggaagt | 840 |
| ggcggggag gctctgatat tcagatgacc cagaccacct ccagcctgtc cgccagcctg | 900 |
| ggcgatcgcg tgaccatctc ttgcagagcc agccaggaca tcagcaagta tctgaattgg | 960 |
| tatcagcaga aacccgacgg caccgtgaag ctgctgatct accacaccag cagactgcac | 1020 |
| tccggcgtgc catccagatt cagcggctct ggctccggca ccgattatag cctgaccatc | 1080 |
| agcaacctgg aacaggaaga tatcgctacc tactttgtc agcaaggcaa caccctgccc | 1140 |
| tacaccttcg gcggaggcac aaaactggaa attaccggca gcaccagcgg cagcggaaag | 1200 |
| cctggaagcg gcgagggaag caccaagggc gaagtgaaac tgcaggaaag cggacccgga | 1260 |

```
ctggtggccc caagccagtc tctgagcgtg acatgtaccg tgtccggcgt gtccctgccc    1320
gactatggcg tgtcctggat caggcagccc cccagaaagg gactggaatg gctgggagtg    1380
atctggggca gcgagacaac ctactacaac agcgccctga agtccaggct gaccattatc    1440
aaggacaact ccaagagcca ggtgttcctg aagatgaaca gcctgcagac cgacgacaca    1500
gccatctact attgcgccaa gcactactac tacggcggca gctacgccat ggactactgg    1560
ggacagggaa cctccgtgac cgtgtcctct accacgacgc cagcgccgcg accaccaaca    1620
ccggcgccca ccatcgcgtc gcagcccctg tccctgcgcc cagaggcgtg ccggccagcg    1680
gcggggggcg cagtgcacac gagggggctg gacttcgcct gtgatatcta catctggggcg    1740 cccttggccg ggacttgtgg ggtccttctc ctgtcactgg ttatcaccct ttactgcaaa    1800
cggggcagaa agaaactcct gtatatattc aaacaaccat ttatgagacc agtacaaact    1860
actcaagagg aagatggctg tagctgccga tttccagaag aagaagaagg aggatgtgaa    1920
ctgagagtga agttcagcag gagcgcagac gcccccgcgt acaagcaggg ccagaaccag    1980
ctctataacg agctcaatct aggacgaaga gaggagtacg atgttttgga caagagacgt    2040
ggccgggacc ctgagatggg gggaaagccg agaaggaaga accctcagga aggcctgtac    2100
aatgaactgc agaaagataa gatggcggag gcctacagtg agattgggat gaaaggcgag    2160
cgccggaggg gcaaggggca cgatggcctt taccagggtc tcagtacagc caccaaggac    2220
acctacgacg cccttcacat gcaggccctg ccccctcgct aa                       2262

<210> SEQ ID NO 33
<211> LENGTH: 45
<212> TYPE: PRT
<213> ORGANISM: Artificial Sequence
<220> FEATURE:
<223> OTHER INFORMATION: Synthetic

<400> SEQUENCE: 33

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 34
<211> LENGTH: 135
<212> TYPE: DNA
<213> ORGANISM: Artificial Sequence
<220> FEATURE:
<223> OTHER INFORMATION: Synthetic

<400> SEQUENCE: 34
accacgacgc cagcgccgcg accaccaaca ccggcgccca ccatcgcgtc gcagcccctg     60
tccctgcgcc cagaggcgtg ccggccagcg gcggggggcg cagtgcacac gagggggctg    120
gacttcgcct gtgat                                                     135

<210> SEQ ID NO 35
<211> LENGTH: 72
<212> TYPE: DNA
<213> ORGANISM: Artificial Sequence
<220> FEATURE:
<223> OTHER INFORMATION: Synthetic

<400> SEQUENCE: 35
```

```
atctacatct gggcgccctt ggccgggact tgtggggtcc ttctcctgtc actggttatc    60 acccttact gc                                                         72

<210> SEQ ID NO 36
<211> LENGTH: 126
<212> TYPE: DNA
<213> ORGANISM: Artificial Sequence
<220> FEATURE:
<223> OTHER INFORMATION: Synthetic

<400> SEQUENCE: 36
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 37
<211> LENGTH: 339
<212> TYPE: DNA
<213> ORGANISM: Artificial Sequence
<220> FEATURE:
<223> OTHER INFORMATION: Synthetic

<400> SEQUENCE: 37
agagtgaagt tcagcaggag cgcagacgcc cccgcgtaca agcagggcca gaaccagctc    60
tataacgagc tcaatctagg acgaagagag gagtacgatg tttttggacaa gagacgtggc   120 cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac caggtctca gtacagccac caaggacacc   300
tacgacgccc ttcacatgca ggccctgccc cctcgctaa                         339

<210> SEQ ID NO 38
<211> LENGTH: 672
<212> TYPE: DNA
<213> ORGANISM: Artificial Sequence
<220> FEATURE:
<223> OTHER INFORMATION: Synthetic

<400> SEQUENCE: 38
accacgacgc cagcgccgcg accaccaaca ccggcgccca ccatcgcgtc gcagcccctg    60
tccctgcgcc cagaggcgtg ccggccagcg gcggggggcg cagtgcacac gaggggctg   120 gacttcgcct gtgatatcta catctgggcg cccttggccg ggacttgtgg ggtccttctc   180
ctgtcactgg ttatcaccct ttactgcaaa cggggcagaa agaaactcct gtatatattc   240
aaacaaccat ttatgagacc agtacaaact actcaagagg aagatggctg tagctgccga   300
tttccagaag aagaagaagg aggatgtgaa ctgagagtga agttcagcag gagcgcagac   360 gccccgcgt acaagcaggg ccagaaccag ctctataacg agctcaatct aggacgaaga   420
gaggagtacg atgttttgga agagacgt ggccgggacc ctgagatggg gggaaagccg   480
agaaggaaga accctcagga aggcctgtac aatgaactgc agaaagataa gatggcggag   540
gcctacagtg agattgggat gaaaggcgag cgccggaggg gcaaggggca cgatggcctt   600
taccagggtc tcagtacagc caccaaggac acctacgacg cccttcacat gcaggccctg   660 cccctcgct aa                                                       672

<210> SEQ ID NO 39
```

<211> LENGTH: 711
<212> TYPE: PRT
<213> ORGANISM: Artificial Sequence
<220> FEATURE:
<223> OTHER INFORMATION: Synthetic

<400> SEQUENCE: 39

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gln Val Gln Leu Gln Gln Ser Gly Pro Gly Leu Val Lys Pro Ser Gln
        115                 120                 125

Thr Leu Ser Leu Thr Cys Ala Ile Ser Gly Asp Ser Val Ser Ser Asn
    130                 135                 140

Ser Ala Ala Trp Asn Trp Ile Arg Gln Ser Pro Ser Arg Gly Leu Glu
145                 150                 155                 160

Trp Leu Gly Arg Thr Tyr Tyr Arg Ser Lys Trp Tyr Asn Asp Tyr Ala
                165                 170                 175

Val Ser Val Lys Ser Arg Ile Thr Ile Asn Pro Asp Thr Ser Lys Asn
            180                 185                 190

Gln Phe Ser Leu Gln Leu Asn Ser Val Thr Pro Glu Asp Thr Ala Val
        195                 200                 205

Tyr Tyr Cys Ala Arg Glu Val Thr Gly Asp Leu Glu Asp Ala Phe Asp
    210                 215                 220

Ile Trp Gly Gln Gly Thr Met Val Thr Val Ser Ser Gly Ser Thr Ser
225                 230                 235                 240

Gly Ser Gly Lys Pro Gly Ser Gly Glu Gly Ser Thr Lys Gly Asp Ile
                245                 250                 255

Gln Met Thr Gln Ser Pro Ser Ser Leu Ser Ala Ser Val Gly Asp Arg
            260                 265                 270

Val Thr Ile Thr Cys Arg Ala Ser Gln Thr Ile Trp Ser Tyr Leu Asn
        275                 280                 285

Trp Tyr Gln Gln Arg Pro Gly Lys Ala Pro Asn Leu Leu Ile Tyr Ala
    290                 295                 300

Ala Ser Ser Leu Gln Ser Gly Val Pro Ser Arg Phe Ser Gly Arg Gly
305                 310                 315                 320

Ser Gly Thr Asp Phe Thr Leu Thr Ile Ser Ser Leu Gln Ala Glu Asp
                325                 330                 335

Phe Ala Thr Tyr Tyr Cys Gln Gln Ser Tyr Ser Ile Pro Gln Thr Phe
            340                 345                 350

Gly Gln Gly Thr Lys Leu Glu Ile Lys Gly Gly Gly Ser Glu Val
        355                 360                 365

Lys Leu Gln Glu Ser Gly Pro Gly Leu Val Ala Pro Ser Gln Ser Leu
    370                 375                 380
```

-continued

```
Ser Val Thr Cys Thr Val Ser Gly Val Ser Leu Pro Asp Tyr Gly Val
385                 390                 395                 400

Ser Trp Ile Arg Gln Pro Pro Arg Lys Gly Leu Glu Trp Leu Gly Val
                405                 410                 415

Ile Trp Gly Ser Glu Thr Thr Tyr Tyr Asn Ser Ala Leu Lys Ser Arg
            420                 425                 430

Leu Thr Ile Ile Lys Asp Asn Ser Lys Ser Gln Val Phe Leu Lys Met
        435                 440                 445

Asn Ser Leu Gln Thr Asp Asp Thr Ala Ile Tyr Tyr Cys Ala Lys His
    450                 455                 460

Tyr Tyr Tyr Gly Gly Ser Tyr Ala Met Asp Tyr Trp Gly Gln Gly Thr
465                 470                 475                 480

Ser Val Thr Val Ser Ser Gly Thr Thr Thr Pro Ala Pro Arg Pro
                485                 490                 495

Pro Thr Pro Ala Pro Thr Ile Ala Ser Gln Pro Leu Ser Leu Arg Pro
                500                 505                 510

Glu Ala Cys Arg Pro Ala Ala Gly Gly Ala Val His Thr Arg Gly Leu
            515                 520                 525

Asp Phe Ala Cys Asp Ile Tyr Ile Trp Ala Pro Leu Ala Gly Thr Cys
530                 535                 540

Gly Val Leu Leu Leu Ser Leu Val Ile Thr Leu Tyr Cys Lys Arg Gly
545                 550                 555                 560

Arg Lys Lys Leu Leu Tyr Ile Phe Lys Gln Pro Phe Met Arg Pro Val
                565                 570                 575

Gln Thr Thr Gln Glu Glu Asp Gly Cys Ser Cys Arg Phe Pro Glu Glu
            580                 585                 590

Glu Glu Gly Gly Cys Glu Leu Arg Val Lys Phe Ser Arg Ser Ala Asp
        595                 600                 605

Ala Pro Ala Tyr Gln Gln Gly Gln Asn Gln Leu Tyr Asn Glu Leu Asn
    610                 615                 620

Leu Gly Arg Arg Glu Glu Tyr Asp Val Leu Asp Lys Arg Arg Gly Arg
625                 630                 635                 640

Asp Pro Glu Met Gly Gly Lys Pro Arg Arg Lys Asn Pro Gln Glu Gly
                645                 650                 655

Leu Tyr Asn Glu Leu Gln Lys Asp Lys Met Ala Glu Ala Tyr Ser Glu
            660                 665                 670

Ile Gly Met Lys Gly Glu Arg Arg Arg Gly Lys Gly His Asp Gly Leu
        675                 680                 685

Tyr Gln Gly Leu Ser Thr Ala Thr Lys Asp Thr Tyr Asp Ala Leu His
    690                 695                 700

Met Gln Ala Leu Pro Pro Arg
705                 710

<210> SEQ ID NO 40
<211> LENGTH: 729
<212> TYPE: PRT
<213> ORGANISM: Artificial Sequence
<220> FEATURE:
<223> OTHER INFORMATION: Synthetic

<400> SEQUENCE: 40

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30
```

```
Ser Ala Ala Trp Asn Trp Ile Arg Gln Ser Pro Ser Arg Gly Leu Glu
    35                  40                  45

Trp Leu Gly Arg Thr Tyr Tyr Arg Ser Lys Trp Tyr Asn Asp Tyr Ala
50                      55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                    85                  90                  95

Tyr Tyr Cys Ala Arg Glu Val Thr Gly Asp Leu Glu Asp Ala Phe Asp
                100                 105                 110

Ile Trp Gly Gln Gly Thr Met Val Thr Val Ser Gly Gly Gly Gly
                115                 120                 125

Ser Asp Ile Gln Met Thr Gln Ser Pro Ser Ser Leu Ser Ala Ser Val
130                 135                 140

Gly Asp Arg Val Thr Ile Thr Cys Arg Ala Ser Gln Thr Ile Trp Ser
145                 150                 155                 160

Tyr Leu Asn Trp Tyr Gln Gln Arg Pro Gly Lys Ala Pro Asn Leu Leu
                165                 170                 175

Ile Tyr Ala Ala Ser Ser Leu Gln Ser Gly Val Pro Ser Arg Phe Ser
                180                 185                 190

Gly Arg Gly Ser Gly Thr Asp Phe Thr Leu Thr Ile Ser Ser Leu Gln
                195                 200                 205

Ala Glu Asp Phe Ala Thr Tyr Tyr Cys Gln Gln Ser Tyr Ser Ile Pro
                210                 215                 220

Gln Thr Phe Gly Gln Gly Thr Lys Leu Glu Ile Lys Gly Gly Gly Gly
225                 230                 235                 240

Ser Gly Gly Gly Gly Ser Gly Gly Gly Gly Ser Gly Gly Gly Gly Ser
                245                 250                 255

Gly Gly Gly Gly Ser Asp Ile Gln Met Thr Gln Thr Thr Ser Ser Leu
                260                 265                 270

Ser Ala Ser Leu Gly Asp Arg Val Thr Ile Ser Cys Arg Ala Ser Gln
    275                 280                 285

Asp Ile Ser Lys Tyr Leu Asn Trp Tyr Gln Gln Lys Pro Asp Gly Thr
    290                 295                 300

Val Lys Leu Leu Ile Tyr His Thr Ser Arg Leu His Ser Gly Val Pro
305                 310                 315                 320

Ser Arg Phe Ser Gly Ser Gly Ser Gly Thr Asp Tyr Ser Leu Thr Ile
                325                 330                 335

Ser Asn Leu Glu Gln Glu Asp Ile Ala Thr Tyr Phe Cys Gln Gln Gly
                340                 345                 350

Asn Thr Leu Pro Tyr Thr Phe Gly Gly Gly Thr Lys Leu Glu Ile Thr
                355                 360                 365

Gly Ser Thr Ser Gly Ser Gly Lys Pro Gly Ser Gly Glu Gly Ser Thr
                370                 375                 380

Lys Gly Glu Val Lys Leu Gln Glu Ser Gly Pro Gly Leu Val Ala Pro
385                 390                 395                 400

Ser Gln Ser Leu Ser Val Thr Cys Thr Val Ser Gly Val Ser Leu Pro
                405                 410                 415

Asp Tyr Gly Val Ser Trp Ile Arg Gln Pro Pro Arg Lys Gly Leu Glu
                420                 425                 430

Trp Leu Gly Val Ile Trp Gly Ser Glu Thr Thr Tyr Tyr Asn Ser Ala
                435                 440                 445
```

```
Leu Lys Ser Arg Leu Thr Ile Ile Lys Asp Asn Ser Lys Ser Gln Val
450                 455                 460

Phe Leu Lys Met Asn Ser Leu Gln Thr Asp Asp Thr Ala Ile Tyr Tyr
465                 470                 475                 480

Cys Ala Lys His Tyr Tyr Tyr Gly Gly Ser Tyr Ala Met Asp Tyr Trp
                485                 490                 495

Gly Gln Gly Thr Ser Val Thr Val Ser Ser Thr Thr Pro Ala Pro
            500                 505                 510

Arg Pro Pro Thr Pro Ala Pro Thr Ile Ala Ser Gln Pro Leu Ser Leu
            515                 520                 525

Arg Pro Glu Ala Cys Arg Pro Ala Ala Gly Gly Ala Val His Thr Arg
530                 535                 540

Gly Leu Asp Phe Ala Cys Asp Ile Tyr Ile Trp Ala Pro Leu Ala Gly
545                 550                 555                 560

Thr Cys Gly Val Leu Leu Leu Ser Leu Val Ile Thr Leu Tyr Cys Lys
                565                 570                 575

Arg Gly Arg Lys Lys Leu Leu Tyr Ile Phe Lys Gln Pro Phe Met Arg
                580                 585                 590

Pro Val Gln Thr Thr Gln Glu Glu Asp Gly Cys Ser Cys Arg Phe Pro
            595                 600                 605

Glu Glu Glu Glu Gly Gly Cys Glu Leu Arg Val Lys Phe Ser Arg Ser
610                 615                 620

Ala Asp Ala Pro Ala Tyr Gln Gln Gly Gln Asn Gln Leu Tyr Asn Glu
625                 630                 635                 640

Leu Asn Leu Gly Arg Arg Glu Glu Tyr Asp Val Leu Asp Lys Arg Arg
                645                 650                 655

Gly Arg Asp Pro Glu Met Gly Gly Lys Pro Arg Arg Lys Asn Pro Gln
                660                 665                 670

Glu Gly Leu Tyr Asn Glu Leu Gln Lys Asp Lys Met Ala Glu Ala Tyr
            675                 680                 685

Ser Glu Ile Gly Met Lys Gly Glu Arg Arg Arg Gly Lys Gly His Asp
            690                 695                 700

Gly Leu Tyr Gln Gly Leu Ser Thr Ala Thr Lys Asp Thr Tyr Asp Ala
705                 710                 715                 720

Leu His Met Gln Ala Leu Pro Pro Arg
                725

<210> SEQ ID NO 41
<211> LENGTH: 232
<212> TYPE: PRT
<213> ORGANISM: Artificial Sequence
<220> FEATURE:
<223> OTHER INFORMATION: Synthetic

<400> SEQUENCE: 41

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80
```

-continued

```
Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Glu Val Lys Leu Gln Glu Ser Gly Pro Gly Leu Val Ala Pro Ser Gln
            115                 120                 125

Ser Leu Ser Val Thr Cys Thr Val Ser Gly Val Ser Leu Pro Asp Tyr
            130                 135                 140

Gly Val Ser Trp Ile Arg Gln Pro Pro Arg Lys Gly Leu Glu Trp Leu
145                 150                 155                 160

Gly Val Ile Trp Gly Ser Glu Thr Thr Tyr Tyr Asn Ser Ala Leu Lys
                165                 170                 175

Ser Arg Leu Thr Ile Ile Lys Asp Asn Ser Lys Ser Gln Val Phe Leu
            180                 185                 190

Lys Met Asn Ser Leu Gln Thr Asp Asp Thr Ala Ile Tyr Tyr Cys Ala
            195                 200                 205

Lys His Tyr Tyr Tyr Gly Gly Ser Tyr Ala Met Asp Tyr Trp Gly Gln
    210                 215                 220

Gly Thr Ser Val Thr Val Ser Ser
225                 230
```

DUAL SPECIFIC ANTI-CD22-ANTI-CD19 CHIMERIC ANTIGEN RECEPTORS

CROSS-REFERENCE TO RELATED APPLICATION

This patent application is a U.S. national stage of PCT/US2016/023055, filed Mar. 18, 2016, which claims the benefit of U.S. Provisional Patent Application No. 62/135,442, filed Mar. 19, 2015, each of which is incorporated by reference in its entirety herein.

STATEMENT REGARDING FEDERALLY SPONSORED RESEARCH AND DEVELOPMENT

This invention was made with Government support under project number ZIA BC 011295 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 61,067 Byte ASCII (Text) file named "730675_ST25.txt" dated Sep. 14, 2017.

BACKGROUND OF THE INVENTION

Cancer is a public health concern. Despite advances in treatments such as chemotherapy, the prognosis for many cancers, including hematological malignancies, may be poor. Accordingly, there exists an unmet need for additional treatments for cancer, particularly hematological malignancies.

BRIEF SUMMARY OF THE INVENTION

An embodiment of the invention provides a dual specific chimeric antigen receptor (CAR) having antigenic specificity for CD19 and CD22, the CAR comprising an anti-CD22 antigen binding domain, an anti-CD19 antigen binding domain, a hinge domain, a transmembrane domain, and an intracellular T cell signaling domain.

Further embodiments of the invention provide related nucleic acids, recombinant expression vectors, host cells, populations of cells, and pharmaceutical compositions relating to the CARs of the invention.

Additional embodiments of the invention provide methods of detecting the presence of cancer in a mammal and methods of treating or preventing cancer in a mammal.

BRIEF DESCRIPTION OF THE SEVERAL VIEWS OF THE DRAWING(S)

FIG. 1 is a graph showing interferon (IFN)-gamma (γ) (pg/mL) secreted by human T cells transduced with an anti-CD19 CAR, green fluorescent protein (GFP), or a dual specific anti-CD19-anti CD22 CAR (SEQ ID NO: 29) ("lenti-CD22-CD19") upon co-culture with target cells K562, K562CD19, K562CD22C2, K562CD22C4, REH, or NALM6.

FIGS. 2A-2D are graphs showing the percentage (%) of target cells NALM6 (diamonds), K562CD19 (squares), K562CD22 (triangles), or K562 (x) that were specifically lysed upon co-culture with human T cells (effector cells) that were untransduced (mock) (A) or transduced with an anti-CD22 CAR (B), an anti-CD19 CAR (C), or a dual specific anti-CD19-anti CD22 CAR (SEQ ID NO: 30) (D) at the indicated effector cell to target cell ratios.

Figure 3:
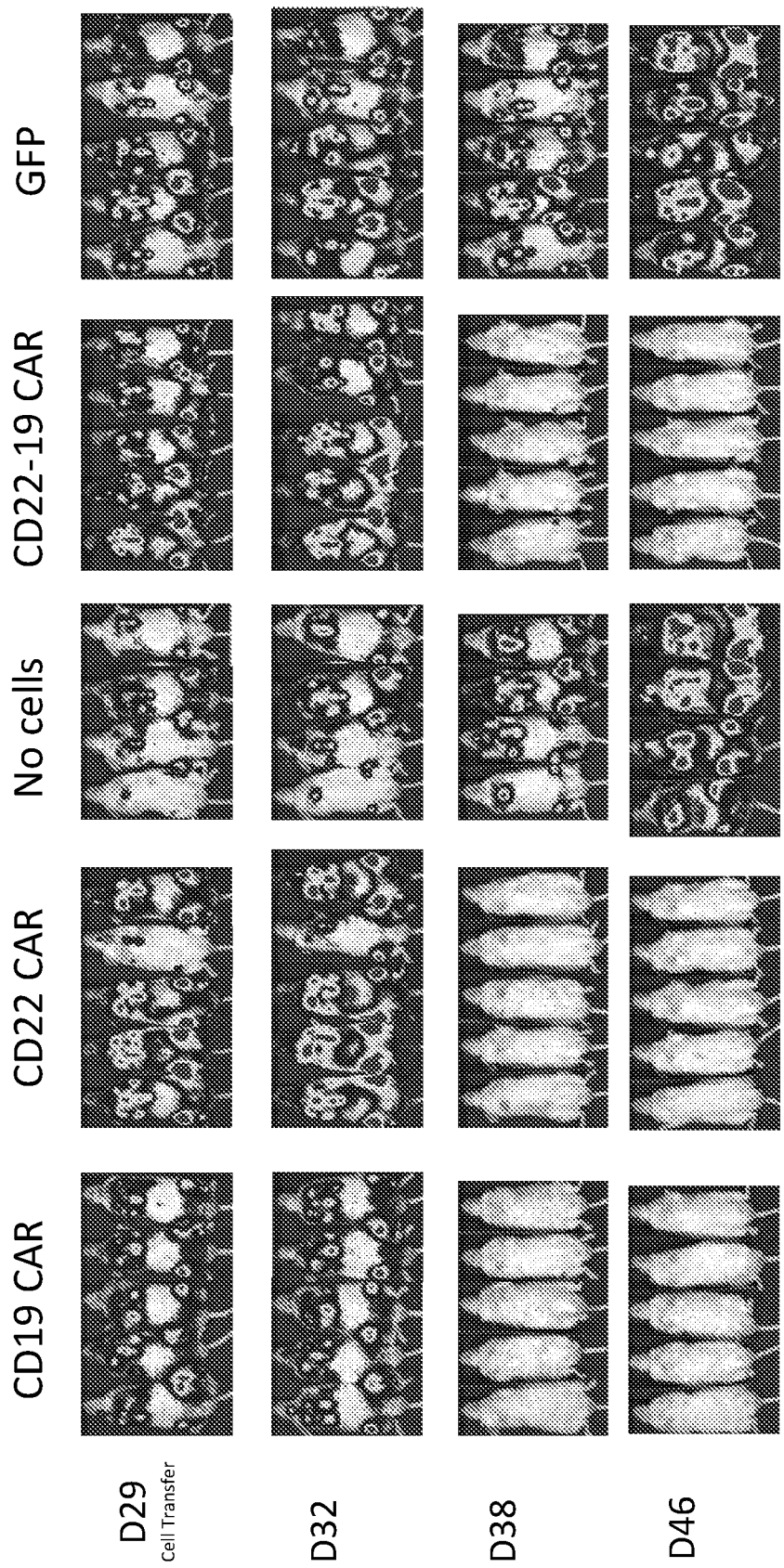

FIG. 3 is a table showing bioluminescent images of mice having human ALL xenograft tumors 29, 32, 38, and 46 days (D) after administration of the xenograft. Mice were treated with T cells transduced with a vector encoding an anti-CD19 CAR, an anti-CD22 CAR, GFP, or a dual specific anti-CD19-anti CD22 CAR (SEQ ID NO: 30) on Day 29 after administration of the xenograft. A change in shading from dark to light indicates decreased tumor burden.

Figure 4:
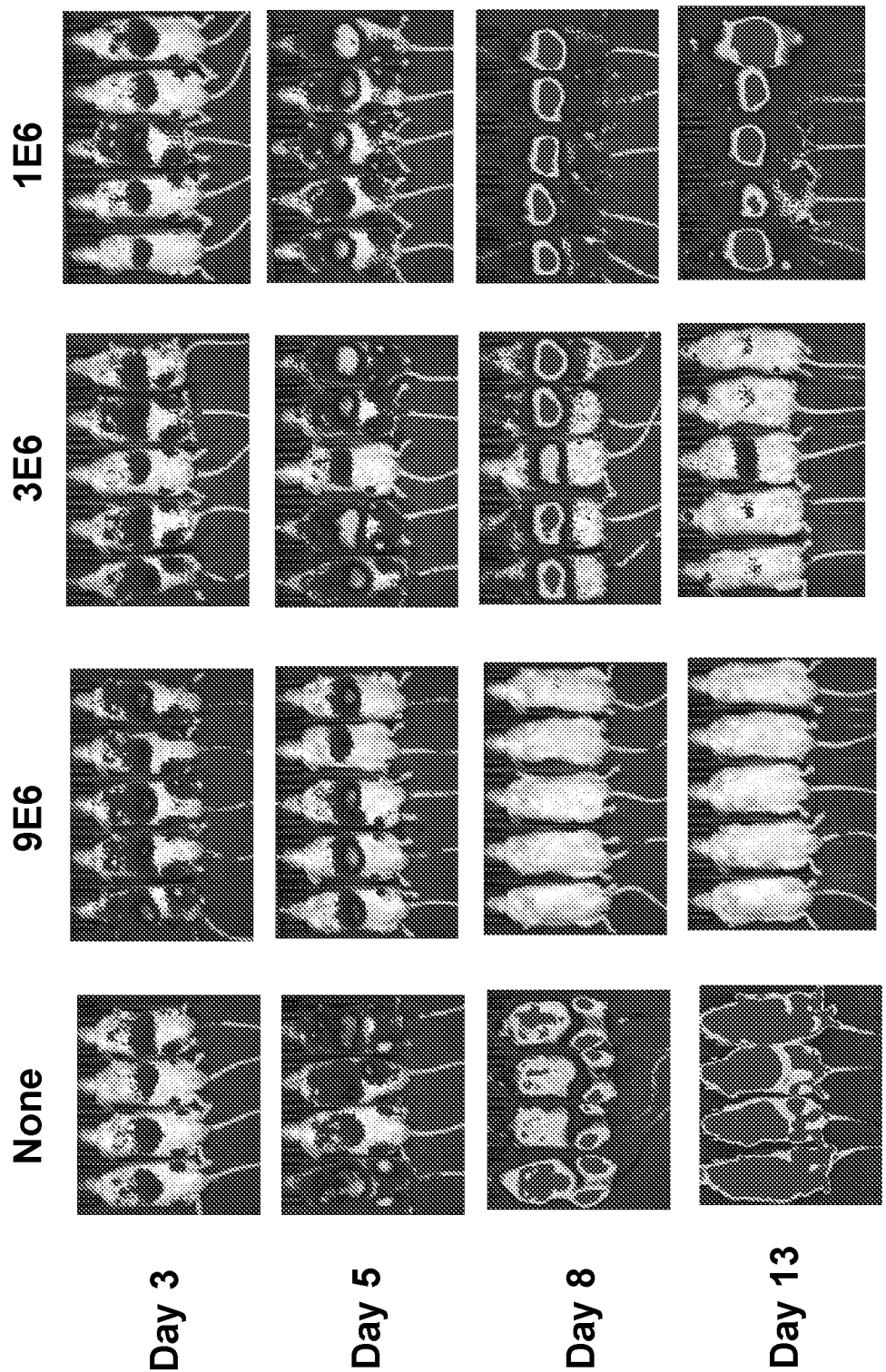

FIG. 4 is a table showing bioluminescent images of mice having human xenograft tumors 3, 5, 8, and 13 days after administration of the xenograft. Mice were treated with no cells or T cells transduced with a vector encoding a dual specific anti-CD19-anti CD22 CAR (SEQ ID NO: 29) ($9 \times 10^6$ cells, $3 \times 10^6$ cells, or $1 \times 10^6$ cells) on Day 3 after administration of the xenograft. A change in shading from dark to light indicates decreased tumor burden.

Figure 5:
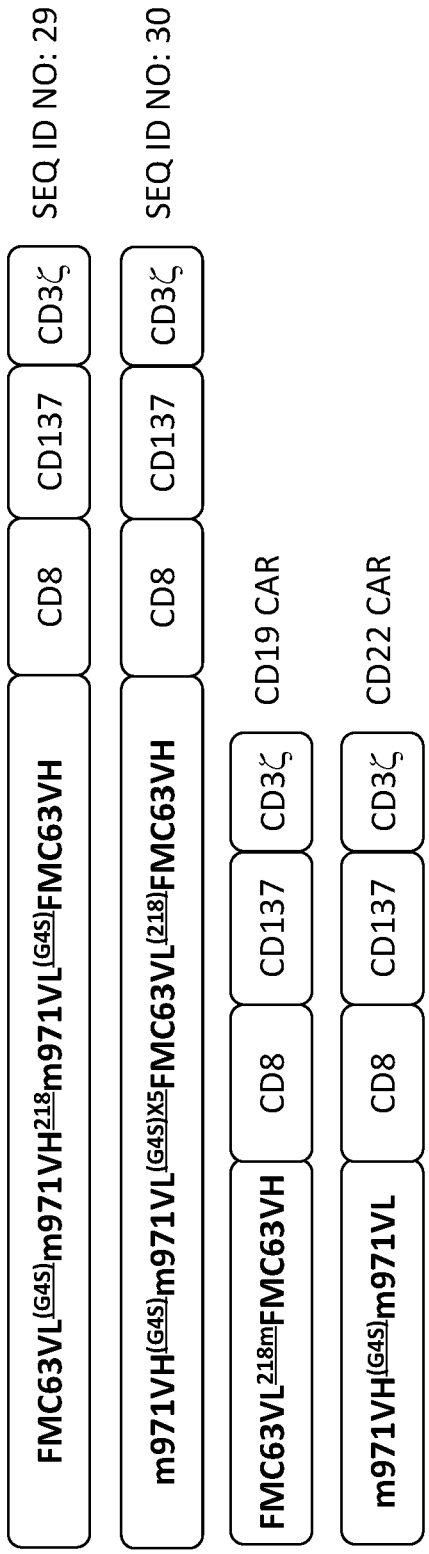

FIG. 5 is a schematic illustrating the components of the dual specific anti-CD19-anti CD22 CARs (SEQ ID NOS: 29 and 30), a CAR having antigenic specificity for only CD19 (anti-CD19 CAR), and a CAR having antigenic specificity for only CD22 (anti-CD22 CAR).

DETAILED DESCRIPTION OF THE INVENTION

An embodiment of the invention provides a dual specific CAR having antigenic specificity for CD19 and CD22, the CAR comprising an anti-CD22 antigen binding domain, an anti-CD19 antigen binding domain, a hinge domain, a transmembrane domain, and an intracellular T cell signaling domain.

A CAR is an artificially constructed hybrid protein or polypeptide containing the antigen binding domains of one or more antibodies (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "antigen(ic) specificity" and "elicit antigen-specific response," as used herein, means that the CAR can specifically bind to and immunologically recognize antigen, such that binding of the CAR to the antigen elicits an immune response.

The phrase "dual specificity" and "dual specific," as used herein, means that the same CAR can specifically bind to and immunologically recognize two different antigens, such that binding of the CAR to at least one of the two antigens elicits an immune response.

The CARs of the invention have antigenic specificity for CD22 and CD19. CD22 is a lineage-restricted B cell antigen belonging to the immunoglobulin (Ig) superfamily. CD22 is expressed in 60-70% of B cell lymphomas and leukemias (e.g., B-chronic lymphocytic leukemia, hairy cell leukemia, acute lymphocytic leukemia (ALL), and Burkitt's lymphoma) and is not present on the cell surface in early stages of B cell development or on stem cells. Vaickus et al., *Crit. Rev. Oncol./Hematol.*, 11:267-297 (1991); Bang et al., *Clin. Cancer Res.*, 11: 1545-50 (2005). CD19 (also known as B-lymphocyte antigen CD19, B4, and CVID3) is a cell surface molecule expressed only by B lymphocytes and follicular dendritic cells of the hematopoietic system. It is the earliest of the B-lineage-restricted antigens to be expressed and is present on most pre-B-cells and most non-T-cell acute lymphocytic leukemia cells and B-cell type chronic lymphocytic leukemia cells (Tedder and Isaacs, *J. Immun.*, 143: 712-717 (1989)).

The inventive dual specific CARs may provide many advantages. For example, the inventive dual specific CARs may, advantageously, provide a greater potency as compared to a CAR that has antigenic specificity for only one of CD19 and CD22 (but not both). The inventive dual specific CARs may also, advantageously, reduce or prevent cancer cell escape due to loss of expression of one of CD19 or CD22 by the cancer cell. For example, it is believed that the inventive dual specific CARs may reduce or prevent relapses that have been observed in cancer patients following treatment with a CAR having antigenic specificity for only CD19 and whose cancer has lost CD19 expression. The inventive dual specific CARs may also increase the patient population that may be successfully treated. For example, a patient that may fail to respond to a CAR therapy that targets only CD19 may respond to a CAR therapy that targets CD22, and a patient that may fail to respond to a CAR therapy that targets only CD22 may respond to a CAR therapy that targets CD19.

Without being bound to a particular theory or mechanism, it is believed that by eliciting an antigen-specific response against CD22 and CD19, the inventive CARs provide for one or more of any of the following: targeting and destroying CD22-expressing cancer cells, targeting and destroying CD19-expressing cancer cells, reducing or eliminating cancer cells, facilitating infiltration of immune cells to tumor site(s), and enhancing/extending anti-cancer responses.

An embodiment of the invention provides a CAR comprising an anti-CD22 antigen binding domain of the m971 antibody ("m971"). The antigen binding domain of m971 specifically binds to CD22. In this regard, a preferred embodiment of the invention provides CARs comprising an anti-CD22 antigen-binding domain comprising, consisting of, or consisting essentially of, a single chain variable fragment (scFv) of the antigen binding domain of m971. The HA22 immunotoxin and the m971 antibody bind to different CD22 epitopes.

The anti-CD22 antigen binding domain may comprise a light chain variable region and/or a heavy chain variable region. In an embodiment of the invention, the heavy chain variable region comprises a CDR1 region, a CDR2 region, and a CDR3 region. In this regard, the anti-CD22 antigen binding domain may comprise one or more of a heavy chain CDR1 region comprising the amino acid sequence of SEQ ID NO: 1; a heavy chain CDR2 region comprising the amino acid sequence of SEQ ID NO: 2; and a heavy chain CDR3 region comprising the amino acid sequence of SEQ ID NO: 3. Preferably, the heavy chain of the anti-CD22 antigen binding domain comprises the amino acid sequences of all of SEQ ID NOs: 1-3.

In an embodiment of the invention, the light chain variable region of the anti-CD22 antigen binding domain may comprise a light chain CDR1 region, a light chain CDR2 region, and a light chain CDR3 region. In this regard, the anti-CD22 antigen binding domain may comprise one or more of a light chain CDR1 region comprising the amino acid sequence of SEQ ID NO: 4; a light chain CDR2 region comprising the amino acid sequence of SEQ ID NO: 5; and a light chain CDR3 region comprising the amino acid sequence of SEQ ID NO: 6. Preferably, the light chain of the anti-CD22 antigen binding domain comprises the amino acid sequences of all of SEQ ID NOs: 4-6. In an especially preferred embodiment, the anti-CD22 antigen binding domain comprises the amino acid sequences of all of SEQ ID NO: 1-6.

The heavy chain variable region of the anti-CD22 antigen binding domain may comprise, consist of, or consist essentially of the amino acid sequence of SEQ ID NO: 13. The light chain variable region of the anti-CD22 antigen binding domain may comprise, consist of, or consist essentially of the amino acid sequence of SEQ ID NO: 14. Accordingly, in an embodiment of the invention, the anti-CD22 antigen binding domain comprises a heavy chain variable region comprising the amino acid sequence of SEQ ID NO: 13 and/or a light chain variable region comprising the amino acid sequence of SEQ ID NO: 14. Preferably, the anti-CD22 antigen binding domain comprises the amino acid sequences of both SEQ ID NOs: 13 and 14.

An embodiment of the invention provides a CAR comprising an anti-CD19 antigen binding domain of the FMC63 antibody ("FMC63"). The antigen binding domain of FMC63 specifically binds to CD19. In this regard, a preferred embodiment of the invention provides CARs comprising an anti-CD19 antigen-binding domain comprising, consisting of, or consisting essentially of, a single chain variable fragment (scFv) of the antigen binding domain of FMC63.

The anti-CD19 antigen binding domain may comprise a light chain variable region and/or a heavy chain variable region. In an embodiment of the invention, the heavy chain variable region of the anti-CD19 antigen binding domain comprises a CDR1 region, a CDR2 region, and a CDR3 region. In this regard, the anti-CD19 antigen binding domain may comprise one or more of a heavy chain CDR1 region comprising the amino acid sequence of SEQ ID NO: 7; a heavy chain CDR2 region comprising the amino acid sequence of SEQ ID NO: 8; and a heavy chain CDR3 region comprising the amino acid sequence of SEQ ID NO: 9. Preferably, the heavy chain of the anti-CD19 antigen binding domain comprises the amino acid sequences of all of SEQ ID NOs: 7-9.

In an embodiment of the invention, the light chain variable region of the anti-CD19 antigen binding domain may comprise a light chain CDR1 region, a light chain CDR2 region, and a light chain CDR3 region. In this regard, the anti-CD19 antigen binding domain may comprise one or more of a light chain CDR1 region comprising the amino acid sequence of SEQ ID NO: 10; a light chain CDR2 region comprising the amino acid sequence of SEQ ID NO: 11; and a light chain CDR3 region comprising the amino acid sequence of SEQ ID NO: 12. Preferably, the light chain of the anti-CD19 antigen binding domain comprises the amino acid sequences of all of SEQ ID NOs: 10-12. In an especially preferred embodiment, the anti-CD19 antigen binding domain comprises the amino acid sequences of all of SEQ ID NO: 7-12.

The heavy chain variable region of the anti-CD19 antigen binding domain may comprise, consist of, or consist essentially of the amino acid sequence of SEQ ID NO: 15. The light chain variable region of the anti-CD19 antigen binding domain may comprise, consist of, or consist essentially of the amino acid sequence of SEQ ID NO: 16. Accordingly, in an embodiment of the invention, the anti-CD19 antigen binding domain comprises a heavy chain variable region comprising the amino acid sequence of SEQ ID NO: 15 and/or a light chain variable region comprising the amino acid sequence of SEQ ID NO: 16. Preferably, the anti-CD19 antigen binding domain comprises the amino acid sequences of both SEQ ID NOs: 15 and 16.

The dual specific CARs have an anti-CD22 antigen binding domain and an anti-CD19 antigen binding domain. In an embodiment of the invention, the CAR comprises all six CDR regions of both of the anti-CD22 antigen binding domain and the anti-CD19 antigen binding domain. In this regard, the CAR may comprise all of SEQ ID NOs: 1-12. In another embodiment of the invention, the CAR comprises the light chain variable region and the heavy chain variable region of both of the anti-CD22 antigen binding domain and the anti-CD19 antigen binding domain. In this regard, the CAR may comprise all of SEQ ID NOs: 13-16.

The anti-CD22 antigen binding domain and the anti-CD19 antigen binding domain may comprise any antigen binding portion of the anti-CD22 or anti-CD19 antibody, respectively. The antigen binding portion can be any portion that has at least one antigen binding site, such as Fab, F(ab')$_2$, dsFv, scFv, diabodies, and triabodies. Preferably, the antigen binding portion is a single-chain variable region fragment (scFv) antibody fragment. An scFv is a truncated Fab fragment including the variable (V) domain of an antibody heavy chain linked to a V domain of a light antibody chain via a synthetic peptide linker, which can be generated using routine recombinant DNA technology techniques. Similarly, disulfide-stabilized variable region fragments (dsFv) can be prepared by recombinant DNA technology.

In an embodiment of the invention, the light chain variable region and the heavy chain variable region of the anti-CD22 antigen binding domain are joined to each other by a linker. The linker may comprise any suitable amino acid sequence. In an embodiment of the invention, the linker is a Gly/Ser linker from about 1 to about 100, from about 3 to about 20, from about 5 to about 30, from about 5 to about 18, or from about 3 to about 8 amino acids in length and consists of glycine and/or serine residues in sequence. Accordingly, the Gly/Ser linker may consist of glycine and/or serine residues. In some embodiments, the Gly/Ser linker is a peptide of the formula: (Xaa1)$_n$, wherein each amino acid residue Xaa1 is selected independently from glycine and serine and n is an integer from 3 to 8. Preferably, the Gly/Ser linker comprises the amino acid sequence of SEQ ID NO: 19. In another embodiment of the invention, the linker comprises the amino acid sequence of SEQ ID NO: 17 (also referred to as "218 linker").

In an embodiment of the invention, the light chain variable region and the heavy chain variable region of the anti-CD19 antigen binding domain are joined to each other by a linker. The linker may be any of the linkers described herein with respect to other aspects of the invention. In an embodiment of the invention, the light chain variable region and the heavy chain variable region of the anti-CD19 antigen binding domain are joined to each other by a linker comprising the amino acid sequence of SEQ ID NO: 17.

In an embodiment, the anti-CD22 antigen binding domain comprises a light chain variable region, a heavy chain variable region, and a linker. In this regard, an embodiment of the anti-CD22 antigen binding domain comprising a light chain variable region, a heavy chain variable region, and the 218 linker comprises, consists of, or consists essentially of, all of SEQ ID NOs: 1-6 and 17; all of SEQ ID NOs: 13, 14, and 17; or SEQ ID NO: 20. An embodiment of the anti-CD22 antigen binding domain comprising a light chain variable region, a heavy chain variable region, and a Gly/Ser linker comprises, consists of, or consists essentially of, all of SEQ ID NOs: 1-6 and 19; all of SEQ ID NOs: 13, 14, and 19; or SEQ ID NO: 21.

In an embodiment, the anti-CD19 antigen binding domain comprises a light chain variable region, a heavy chain variable region, and a linker. In this regard, an embodiment of the anti-CD19 antigen binding domain comprising a light chain variable region, a heavy chain variable region, and the 218 linker comprises, consists of, or consists essentially of, all of SEQ ID NOs: 7-12 and 17; all of SEQ ID NOs: 15-17; or SEQ ID NO: 22. An embodiment of the anti-CD19 antigen binding domain comprising a light chain variable region, a heavy chain variable region, and a Gly/Ser linker comprises, consists of, or consists essentially of, all of SEQ ID NOs: 7-12 and 19; all of SEQ ID NOs: 15, 16, and 19; or SEQ ID NO: 41.

In an embodiment of the invention, the anti-CD19 antigen binding domain and the anti-CD22 antigen binding domain are joined to each other by a linker. The linker may comprise any suitable amino acid sequence. The linker may, for example, comprise any of the linkers described herein with respect to other aspects of the invention. Preferably, the linker joining the anti-CD19 antigen binding domain and the anti-CD22 antigen binding domain to each other comprises a Gly/Ser linker which is a peptide of the formula [GGGGS (SEQ ID NO: 19)]$_m$, wherein in is an integer from 1 to 10, from 2 to 8, or from 3 to 5. Preferably, m is 5. Preferably, the linker joining the anti-CD19 antigen binding domain and the anti-CD22 antigen binding domain to each other comprises the amino acid sequence of SEQ ID NO: 18. In this regard, the anti-CD19 antigen binding domain and the anti-CD22 antigen binding domain that are joined to each other by a linker comprises the amino acid sequence of SEQ ID NO: 24 (comprising m971 heavy and light chains that are joined by a Gly/Ser linker and FMC63 heavy and light chains that are joined by the 218 linker, with the linker of SEQ ID NO: 18 positioned between the anti-CD22 and anti-CD19 antigen binding domains). While the anti-CD19 antigen binding domain may be positioned adjacent to the amino terminus of the anti-CD22 antigen binding domain (with a linker positioned between them), in an embodiment of the invention, the anti-CD22 antigen binding domain is positioned adjacent to the amino terminus of the anti-CD19 antigen binding domain (with a linker positioned between them).

The heavy and light chains of the anti-CD19 and anti-CD22 antigen binding domains may be positioned in any suitable orientation with any of the linkers described herein positioned between the heavy and light chains. In an embodiment of the invention, the CAR comprises (i) the FMC63 light chain positioned adjacent to the amino terminus of the m971 heavy chain with a linker positioned between them, (ii) the m971 heavy chain positioned adjacent to the amino terminus of the m971 light chain with a linker positioned between them, and (iii) the m971 light chain positioned adjacent to the amino terminus of the FMC63 heavy chain with a linker positioned between them (for example, SEQ ID NO: 23 and SEQ ID NO: 29 and 39, described in more detail below). In another embodiment of the invention, the CAR comprises (i) the m971 heavy chain positioned adjacent to the amino terminus of the m971 light chain with a linker positioned between them, (ii) the m971 light chain positioned adjacent to the amino terminus of the FMC63 light chain with a linker positioned between them, and (iii) the FMC63 light chain positioned adjacent to the amino terminus of the FMC63 heavy chain with a linker positioned between them (for example, SEQ ID NO: 24 and SEQ ID NO: 30 and 40, described in more detail below).

In an embodiment, the antigen binding domain comprises a leader sequence. In an embodiment of the invention, the leader sequence may be positioned at the amino terminus of the light chain variable region of the anti-CD19 antigen binding domain (e.g., at the amino terminus of the FMC63 light chain). In another embodiment of the invention, the leader sequence is positioned at the amino terminus of the light chain variable region of the anti-CD22 antigen binding domain (e.g., at the amino terminus of the m971 heavy chain). The leader sequence may comprise any suitable leader sequence. In an embodiment, the leader sequence comprises, consists of, or consists essentially of the amino acid sequence of SEQ ID NO: 25. In an embodiment of the invention, while the leader sequence may facilitate expression of the CAR on the surface of the cell, the presence of the leader sequence in an expressed CAR is not necessary in order for the CAR to function. In an embodiment of the invention, upon expression of the CAR on the cell surface, the leader sequence may be cleaved off of the CAR. Accordingly, in an embodiment of the invention, the CAR lacks a leader sequence.

In an embodiment of the invention, the CAR comprises a hinge domain. In an embodiment of the invention, the hinge domain is a CD8 hinge domain. In a preferred embodiment, the CD8 hinge domain is human. Preferably, the CD8 hinge domain comprises, consists of, or consists essentially of SEQ ID NO: 33.

In an embodiment of the invention, the CAR comprises a transmembrane (TM) domain. In an embodiment of the invention, the TM domain is a CD8 TM domain. In a preferred embodiment, the CD8 TM domain is human. Preferably, the CD8 TM domain comprises, consists of, or consists essentially of SEQ ID NO: 26.

In an embodiment of the invention, the CAR comprises an intracellular T cell signaling domain. In an embodiment of the invention, the intracellular T cell signaling domain comprises a 4-1BB intracellular T cell signaling sequence. 4-1BB, also known as CD137, transmits a potent costimulatory signal to T cells, promoting differentiation and enhancing long-term survival of T lymphocytes. Preferably, the 4-1BB intracellular T cell signaling sequence is human. In a preferred embodiment, the 4-1BB intracellular T cell signaling sequence comprises, consists of, or consists essentially of the amino acid sequence of SEQ ID NO: 27.

In an embodiment of the invention, the intracellular T cell signaling domain comprises a CD3 zeta (ζ) intracellular T cell signaling sequence. CD3ζ associates with TCRs to produce a signal and contains immunoreceptor tyrosine-based activation motifs (ITAMs). Preferably, the CD3ζ intracellular T cell signaling sequence is human. In a preferred embodiment, the CD3ζ intracellular T cell signaling sequence comprises, consists of, or consists essentially of the amino acid sequence of SEQ ID NO: 28, wherein X at position 14 is glutamine or lysine.

Additional embodiments of the invention provide full-length CARs comprising, consisting of, or consisting essentially of any of, the amino acid sequences set forth in Table 1.

TABLE 1

| | | Components | |
|---|---|---|---|
| Full length CAR sequence | Sequence providing the anti-CD19 and anti-CD22 antigen binding domains | Transmembrane and Signaling Domains | |
| SEQ ID NO: 29 | SEQ ID NO: 23 | CD8 hinge domain (SEQ ID NO: 33), CD8 TM domain (SEQ ID NO: 26), 4-1BB intracellular T cell signaling sequence (SEQ ID NO: 27), and CD3ζ intracellular T cell signaling sequence (SEQ ID NO: 28, wherein X at position 14 is Lys) | |
| SEQ ID NO: 30 | SEQ ID NO: 24 | CD8 hinge domain (SEQ ID NO: 33), CD8 TM domain (SEQ ID NO: 26), 4-1BB intracellular T cell signaling sequence (SEQ ID NO: 27), and CD3ζ intracellular T cell signaling sequence (SEQ ID NO: 28, wherein X at position 14 is Lys) | |
| SEQ ID NO: 39 | SEQ ID NO: 23 | CD8 hinge domain (SEQ ID NO: 33), CD8 TM domain (SEQ ID NO: 26), 4-1BB intracellular T cell signaling sequence (SEQ ID NO: 27), and CD3ζ intracellular T cell signaling sequence (SEQ ID NO: 28, wherein X at position 14 is Gln) | |
| SEQ ID NO: 40 | SEQ ID NO: 24 | CD8 hinge domain (SEQ ID NO: 33), CD8 TM domain (SEQ ID NO: 26), 4-1BB intracellular T cell signaling sequence (SEQ ID NO: 27), and CD3ζ intracellular T cell signaling sequence (SEQ ID NO: 28, wherein X at position 14 is Gln) | |

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent cancer, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 90%, about 91%, about 92%, about 93%, about 94%, about 95%, about 96%, about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins, including de novo synthesis. Also, the CARs can be recombinantly produced using the nucleic acids described herein using standard recombinant methods. See, for instance, Green et al., *Molecular Cloning: A Laboratory Manual*, 4th ed., Cold Spring Harbor Press, Cold Spring Harbor, N.Y. 2012. Further, portions of some of the CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive CARs can be synthetic, recombinant, isolated, and/or purified.

Further provided by an embodiment of the invention is a nucleic acid comprising a nucleotide sequence encoding any of the CARs described herein (including functional portions and functional variants thereof). The nucleic acids of the invention may comprise a nucleotide sequence encoding any of the leader sequences, antigen binding domains, transmembrane domains, linkers, and/or intracellular T cell signaling domains described herein.

In an embodiment, the nucleic acid comprises a nucleotide sequence that encodes a leader sequence, anti-CD22 and anti-CD19 antigen binding domains (including a light chain variable region and a heavy chain variable region joined by linkers), a CD8 hinge domain, a CD8 transmembrane domain, a 4-1BB intracellular T cell signaling domain, and a CD3ζ intracellular T cell signaling domain. For example, the nucleic acid may comprise a nucleotide sequence that encodes anti-CD22 and anti-CD19 antigen binding domains (including a light chain variable region and a heavy chain variable region joined by linkers), a CD8 hinge domain (SEQ ID NO: 34), a CD8 transmembrane domain (SEQ ID NO: 35), a 4-1BB intracellular T cell signaling domain (SEQ ID NO: 36), and a CD3ζ intracellular T cell signaling domain (SEQ ID NO: 37). In an embodiment of the invention, the nucleic acid comprises a nucleotide sequence that encodes a CD8 hinge domain, a CD8 transmembrane domain, a 4-1BB intracellular T cell signaling domain, and a CD3ζ intracellular T cell signaling domain comprising the nucleotide sequence of SEQ ID NO: 38. In an embodiment of the invention, the nucleic acid may comprise, consist of, or consist essentially of, the nucleotide sequence of SEQ ID NO: 31 or 32, which encodes a full-length CAR comprising the amino acid sequence of SEQ ID NO: 29 or 30, respectively.

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the CAR and which may or may not be translated upon expression of the nucleic acid by a host cell.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green et al., supra. The nucleic acids can be constructed based on chemical synthesis and/or enzymatic ligation reactions using procedures known in the art. See, for example, Green et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector.

In an embodiment, the recombinant expression vectors of the invention can be prepared using standard recombinant DNA techniques described in, for example, Green et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may also comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the inventive CARs (including any of the functional portions or variants thereof), nucleic acids, recombinant expression vectors, host cells, or populations of host cells. Conjugates, as well as methods of synthesizing conjugates in general, are known in the art.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating cells, memory T cells, naïve T cells, and the like. The T cell may be a CD8$^+$ T cell or a CD4$^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The inventive CARs (including functional portions and variants thereof), nucleic acids, recombinant expression vectors, and host cells (including populations thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the inventive CAR materials described herein, and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Methods for preparing administrable (e.g., parenterally administrable) compositions are known or apparent to those skilled in the art and are described in more detail in, for example, *Remington: The Science and Practice of Pharmacy*, Pharmaceutical Press; 22nd ed. (2012).

The inventive CAR materials may be administered in any suitable manner. Preferably, the inventive CAR materials are administered by injection, (e.g., subcutaneously, intravenously, intratumorally, intraarterially, intramuscularly, intradermally, interperitoneally, or intrathecally). Preferably, the inventive CAR materials are administered intravenously. A suitable pharmaceutically acceptable carrier for the inventive CAR material for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration. By way of example and not intending to limit the invention, when the inventive CAR material is a host cell, an exemplary dose of host cells may be a minimum of one million cells (1×10$^6$ cells/dose).

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent cancer in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously. An exemplary therapeutic agent that can be co-administered with the CAR materials is IL-2. It is believed that IL-2 enhances the therapeutic effect of the inventive CAR materials.

It is contemplated that the inventive CAR materials can be used in methods of treating or preventing a disease in a mammal. Without being bound to a particular theory or mechanism, the inventive CAR materials have biological activity, e.g., ability to recognize antigen, e.g., one or both of CD19 and CD22, such that the CAR when expressed by a cell is able to mediate an immune response against the cell expressing the antigen, e.g., one or both of CD19 and CD22, for which the CAR has dual specificity. In this regard, an embodiment of the invention provides a method of treating or preventing cancer in a mammal, comprising administering to the mammal any of the CARs, the nucleic acids, the recombinant expression vectors, the host cells, the population of cells, and/or the pharmaceutical compositions of the invention in an amount effective to treat or prevent cancer in the mammal.

An embodiment of the invention further comprises lymphodepleting the mammal prior to administering the inventive CAR materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the tem' "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia (CLL), chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, non-Hodgkin lymphoma, B-chronic lymphocytic leukemia, B-precursor acute lymphoblastic leukemia (B-ALL), pre-B cell precursor acute lymphoblastic leukemia (BCP-ALL), B cell lymphoma, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is a hematological malignancy (e.g., leukemia or lymphoma, including but not limited to Hodgkin lymphoma, non-Hodgkin lymphoma, CLL, acute lymphocytic cancer, acute myeloid leukemia, B-chronic lymphocytic leukemia, hairy cell leukemia, acute lymphocytic leukemia (ALL) (also referred to as "acute lymphoblastic leukemia"), B-ALL, BCP-ALL, B cell lymphoma, and Burkitt's lymphoma). Preferably, the cancer is characterized by the expression of one or both of CD22 and CD19, and more preferably is a hematological malignancy that is characterized by the expression of one or both of CD19 and CD22.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a use of the inventive CARs, nucleic acids, recombinant expression vectors, host cells, populations of cells, or pharmaceutical compositions, for the treatment or prevention of cancer in a mammal.

Another embodiment of the invention provides a method of detecting the presence of cancer in a mammal, comprising: (a) contacting a sample comprising one or more cells from the mammal with the CARs, the nucleic acids, the recombinant expression vectors, the host cells, the population of cells, or the pharmaceutical compositions of the invention, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor α (TNF-α) or interleukin 2 (IL-2)). In addition, CAR function can be evaluated by measurement of cellular cytotoxicity, as described in Zhao et al., *J. Immunol.*, 174: 4415-4423 (2005).

The following examples further illustrate the invention but, of course, should not be construed as in any way limiting its scope.

Example 1

This example demonstrates the expression of dual specific anti-CD19-anti CD22 CARs by human T cells.

Human T cells were transduced with a lentiviral vector encoding a dual specific anti-CD19-anti CD22 CAR comprising the amino acid sequence of SEQ ID NO: 29 or a retroviral vector encoding a dual specific anti-CD19-anti CD22 CAR comprising the amino acid sequence of SEQ ID NO: 30. As controls, human T cells were not transduced (mock-treated cells) or were transduced with a vector encoding a CAR having antigenic specificity for only CD19 (anti-CD19 CAR) or a CAR having antigenic specificity for only CD22 (anti-CD22 CAR) (see FIG. 5).

CAR expression by CD3+ cells was evaluated by flow cytometry. Expression of the anti-CD19 CAR was detected using an anti-CD19 idiotype antibody, and expression of the anti-CD22 CAR was detected using a CD22 Fc construct. No expression of anti-CD19 CAR or anti-CD22 CAR was detected in the mock-treated cells. Expression of the anti-CD19 CAR, but not the anti-CD22 CAR, was detected in the cells transduced with a vector encoding the anti-CD19 CAR. Expression of the anti-CD22 CAR, but not the anti-CD19 CAR, was detected in the cells transduced with a vector encoding the anti-CD22 CAR. Both anti-CD19 and anti-CD22 CAR expression was detected in cells transduced with a vector encoding either dual specific anti-CD19-anti CD22 CAR, SEQ ID NO: 29 or 30.

CAR expression relative to CD3 expression was also evaluated by flow cytometry. The percentages of cells expressing CD3, anti-CD19 CAR, and anti-CD22 CAR are shown in Tables 2A and 2B.

TABLE 2A

| Phenotype | Cells transduced with anti-CD19 CAR (%) | Cells transduced with dual specific anti-CD19-anti CD22 CAR SEQ ID NO: 29 (%) |
|---|---|---|
| anti-CD19 CAR+/CD3+ | 53.1 | 71.6 |
| anti-CD19 CAR+/CD3− | 23.7 | 13.6 |
| anti-CD19 CAR−/CD3+ | 23.2 | 14.4 |
| anti-CD19 CAR−/CD3− | 0.0 | 0.3 |

TABLE 2B

| Phenotype | Untransduced cells (Mock) | Cells transduced with dual specific anti-CD19-anti CD22 CAR SEQ ID NO: 29 (%) |
|---|---|---|
| anti-CD22 CAR+/CD3+ | 0 | 67.7 |
| anti-CD22 CAR+/CD3− | 0 | 13.5 |
| anti-CD22 CAR−/CD3+ | 0 | 17.8 |
| anti-CD22 CAR−/CD3− | 100 | 1.0 |

Example 2

This example demonstrates that human cells transduced with a vector encoding a dual specific anti-CD19-anti CD22 CAR produce cytokine upon co-culture with CD19+/CD22+, CD19−/CD22+, or CD19+/CD22− target cells.

Human T cells were transduced with a lentiviral vector encoding an anti-CD19 CAR, green fluorescent protein (GFP), or a dual specific anti-CD19-anti CD22 CAR (SEQ ID NO: 29) (see FIG. 5). Tranduced cells were incubated with the target cells listed in Table 3 below for 12 hours. The supernatants were assayed for interferon (IFN)-gamma (γ) secretion by enzyme-linked immunosorbent assay (ELISA).

TABLE 3

| Target Cell | Phenotype |
|---|---|
| K562 | CD19−/CD22− |
| K562CD19 | CD19+/CD22− |
| K562CD22C2 | CD19−/CD22+ |
| K562CD22C4 | CD19−/CD22+ |
| NALM6 (B ALL cell line) | CD19+/CD22+ |
| REH (B ALL cell line) | CD19+/CD22+ |

The results are shown in FIG. 1. As shown in FIG. 1, human cells transduced with a vector encoding the dual specific anti-CD19-anti CD22 CAR (SEQ ID NO: 29) produced cytokine upon co-culture with CD19+/CD22+, CD19−/CD22+, or CD19+/CD22− target cells.

Example 3

This example demonstrates that human cells transduced with a vector encoding a dual specific anti-CD19-anti CD22 CAR lyse CD19+/CD22+, CD19−/CD22+, or CD19+/CD22− target cells in vitro.

Human T cells were untransduced (mock) or were transduced with a lentiviral vector encoding an anti-CD19 CAR, an anti-CD22 CAR, or a dual specific anti-CD19-anti CD22 CAR (SEQ ID NO: 30) (see FIG. 5). The transduced cells were incubated with $Cr^{51}$-labeled target cells NALM6, K562, K562CD19, or K562CD22 (CD19−/CD22+) for four hours. Target cell killing was measured by chromium release assay. The results are shown in FIGS. 2A-2D.

As shown in FIGS. 2A-2D, human cells transduced with a vector encoding the dual specific anti-CD19-anti CD22 CAR (SEQ ID NO: 30) specifically lysed CD19+/CD22+, CD19−/CD22+, or CD19+/CD22− target cells in vitro as measured by chromium release assay.

Example 4

This example demonstrates that human cells transduced with a vector encoding a dual specific anti-CD19-anti CD22 CAR promote the regression of a CD19+/CD22+ human tumor xenograft in mice.

NSG (immunodeficient) mice were injected with a luciferase-expressing, patient-derived ALL xenograft (CD19+/CD22+, $1 \times 10^6$ cells) intravenously on day 0. On day 29 following administration of the xenograft, the mice were injected with $5 \times 10^6$ T cells transduced with a vector encoding an anti-CD19 CAR, an anti-CD22 CAR, GFP, or a dual specific anti-CD19-anti CD22 CAR (SEQ ID NO: 30) (see FIG. 5). Control mice were administered the xenograft but received no transduced cells. Mice were imaged on Days 29, 32, 38, and 46 following administration of the xenograft. The results are shown in FIG. 3. A change in shading from dark to light indicates decreased tumor burden in FIG. 3. As shown in FIG. 3, mice that were administered cells transduced with a vector encoding the dual specific anti-CD19-anti CD22 CAR (SEQ ID NO: 30) demonstrated a dramatically reduced tumor burden by Day 38.

Example 5

This example demonstrates a dose titration of human cells transduced with a vector encoding a dual specific anti-CD19-anti CD22 CAR.

NSG (immunodeficient) mice were injected with a luciferase-expressing, NALM6-GL xenograft (CD19+/CD22+, $1 \times 10^6$ cells) intravenously on day 0. On day 3 following administration of the xenograft, the mice were injected with $9 \times 10^6$, $3 \times 10^6$, or $1 \times 10^6$ T cells transduced with a vector encoding a dual specific anti-CD19-anti CD22 CAR (SEQ ID NO: 29). Control mice were administered the xenograft but received no transduced cells. Mice were imaged on Days 3, 5, 8, and 13 following administration of the xenograft. The results are shown in FIG. 4. A change in shading from dark to light indicates decreased tumor burden in FIG. 4. As shown in FIG. 4, a dose of at least $3 \times 10^6$ CAR-transduced T cells was effective to promote the regression of a CD19+/CD22+ human tumor xenograft in mice.

Example 6

This example demonstrates that the off-target toxicity of human cells transduced with a vector encoding a dual specific anti-CD19-anti CD22 CAR is minimal or absent.

Human T cells ($1 \times 10^5$) transduced with a lentiviral vector encoding a dual specific anti-CD19-anti CD22 CAR (SEQ ID NO: 29; referred to as "CAR1" in Table 4) or GFP (referred to as "Lenti-GFP" in Table 4) were washed and co-cultured with the target cells ($1 \times 10^5$) listed in Table 4 in a 37° C. incubator for 16 hours. The culture supernatant was harvested and IFN-γ production was measured using ELISA. The transduced T cells alone were used as negative controls. K562 is a chronic myelogenous leukemia cell line which does not express CD19 or CD22. Each of REH-TSLPR and NALM6 are patient-derived leukemia cell lines which express both CD19 and CD22. These two cell lines were used as positive controls. All testing was done in triplicate. The results are shown in Table 4.

TABLE 4

| Sample | IFN-γ pg/ml |
| --- | --- |
| Lenti-GFP | 23.504 |
| Lenti-GFP+ MSC-BMSC | 18.105 |
| Lenti-GFP+ HUVEC-Endothelial | 23.493 |
| Lenti-GFP+ Cardiomyocyte | 23.084 |
| Lenti-GFP+ iPSC-Neuron | 30.459 |
| Lenti-GFP+ CCD19lu_Fibroblast | 32.091 |
| Lenti-GFP+ MOVAS_Fibroblast | 37.544 |
| CAR1 | 121.622 |
| CAR1+ MSC-BMSC | 199.834 |
| CAR1+ HUVEC-Endothelial | 132.046 |
| CAR1+ Cardiomyocyte | 1193.77 |
| CAR1+ iPSC-Neuron | 160.536 |
| CAR1+ CCD19lu_Fibroblast | 179.856 |
| CAR1+ MOVAS_Fibroblast | 162.186 |
| Lenti-GFP+ SW403-Colon | 17.287 |
| Lenti-GFP+ 293T-Kindney | 19.883 |
| Lenti-GFP+ H1299-Lung | 24.434 |
| Lenti-GFP+ K562 | 60.509 |
| Lenti-GFP+ Melanoma-Skin | 84.876 |
| Lenti-GFP+ REH-TSLPR | 306.269 |
| Lenti-GFP+ NALM6 | 428.032 |
| CAR1+ SW403-Colon | 114.366 |
| CAR1+ 293T-Kindney | 52.529 |
| CAR1+ H1299-Lung | 80.015 |
| CAR1+ Melanoma-skin | 249.743 |
| CAR1+ K562 | 120.395 |
| CAR1+ REH-TSLPR | 28462.6 |
| CAR1+ NALM6 | 52065.8 |

As shown in Table 4, human T cells transduced with a dual specific anti-CD19-anti CD22 CAR (SEQ ID NO: 29) demonstrated little or no toxicity toward cells other than the CD19+/CD22+ REH-TSLPR and NALM6 cell lines.

Example 7

This example demonstrates that human cells transduced with a vector encoding a dual specific anti-CD19-anti CD22 CAR produce intracellular IFN-γ in response to co-culture with CD19+ or CD22+ target cells.

Human T cells were transduced with a vector encoding an anti-CD19 CAR, an anti-CD22 CAR, or a dual specific anti-CD19-anti CD22 CAR (SEQ ID NO: 30). The transduced cells were co-cultured with the target cells listed in Table 5 for 4 hours. As a negative control, the transduced cells were co-cultured with K562 (CD19−/CD22−) for 4 hours. The co-cultured cells were then harvested for analysis. The cells were stained for the surface marker CD8 and intracellular IFN-γ and were subsequently analyzed by flow cytometry. The results are shown in Table 5.

TABLE 5

| Effector cell | Target Cell | % IFN-γ positive |
| --- | --- | --- |
| anti-CD19 CAR | K562-19 | 22.2 |
|  | K562 | 0.8 |
| anti-CD22 CAR | K562-22 | 55.6 |
|  | K562 | 0.4 |

TABLE 5-continued

| Effector cell | Target Cell | % IFN-γ positive |
|---|---|---|
| dual specific anti-CD19-anti CD22 CAR (SEQ ID NO: 30) | K562-19 | 25 |
| | K562-22 | 30 |
| | K562 | 0.6 |

As shown in Table 5, human cells transduced with a vector encoding a dual specific anti-CD19-anti CD22 CAR produced intracellular IFN-γ in response to co-culture with CD19+ or CD22+ target cells.

All references, including publications, patent applications, and patents, cited herein are hereby incorporated by reference to the same extent as if each reference were individually and specifically indicated to be incorporated by reference and were set forth in its entirety herein.

The use of the ten is "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A dual specific chimeric antigen receptor (CAR) having antigenic specificity for CD19 and CD22, the CAR comprising an anti-CD22 antigen binding domain, an anti-CD19 antigen binding domain, a hinge domain, a transmembrane domain, and an intracellular T cell signaling domain, wherein the CAR comprises the amino acid sequence of SEQ ID NO: 23 or SEQ ID NO: 24.

2. The CAR according to claim 1, wherein the CAR comprises the amino acid sequence of SEQ ID NO: 23.

3. The CAR according to claim 1, wherein the CAR comprises the amino acid sequence of SEQ ID NO: 24.

4. The CAR according to claim 1, comprising the amino acid sequence of SEQ ID NO: 29.

5. The CAR according to claim 1, comprising the amino acid sequence of SEQ ID NO: 39.

6. The CAR according to claim 1, comprising the amino acid sequence of SEQ ID NO: 30.

7. The CAR according to claim 1, comprising the amino acid sequence of SEQ ID NO: 40.

8. The CAR according to claim 1, wherein the CAR comprises a CD8 transmembrane domain and a CD8 hinge domain.

9. The CAR according to claim 8, wherein the CD8 transmembrane domain comprises the amino acid sequence of SEQ ID NO: 26 and the CD8 hinge domain comprises the amino acid sequence of SEQ ID NO: 33.

10. The CAR according to claim 1, wherein the intracellular T cell signaling domain comprises a 4-1BB intracellular T cell signaling sequence.

11. The CAR according to claim 1, wherein the intracellular T cell signaling domain comprises a CD3 zeta (ζ) intracellular T cell signaling sequence.

12. The CAR according to claim 10, wherein the 4-1BB intracellular T cell signaling sequence comprises the amino acid sequence of SEQ ID NO: 27.

13. The CAR according to claim 11, wherein the CD3ζ intracellular T cell signaling sequence comprises the amino acid sequence of SEQ ID NO: 28.

14. A pharmaceutical composition comprising a population of cells expressing the CAR of claim 1, and a pharmaceutically acceptable carrier.

15. The pharmaceutical composition of claim 14, wherein the CAR comprises the amino acid sequence of SEQ ID NO: 29 or SEQ ID NO: 39.

16. A nucleic acid comprising a nucleotide sequence encoding the CAR of claim 1.

17. The nucleic acid according to claim 16, comprising the nucleotide sequence of SEQ ID NO: 31 or 32.

18. A recombinant expression vector comprising the nucleic acid of claim 16.

19. An isolated host cell comprising the recombinant expression vector of claim 18.

20. A population of cells comprising at least one host cell of claim 19.

21. A nucleic acid comprising a nucleotide sequence encoding a CAR of claim 5.

22. A method of treating a hematological malignancy in a human patient in need thereof, the method comprising administering to the patient a population of T cells expressing a nucleic acid encoding the CAR of claim 1 in an amount effective to treat the malignancy.

23. A method of treating a hematological malignancy in a human patient in need thereof, the method comprising administering to the patient a population of T cells expressing a nucleic acid encoding the CAR of claim 4 in an amount effective to treat the malignancy.

24. A method of treating a hematological malignancy in a human patient in need thereof, the method comprising administering to the patient a population of T cells expressing a nucleic acid encoding the CAR of claim 5 in an amount effective to treat the malignancy.

* * * * *